(12) United States Patent
Pionetti et al.

(10) Patent No.: US 10,486,367 B2
(45) Date of Patent: Nov. 26, 2019

(54) DEVICE AND METHOD FOR INSTALLING A TUBULAR JOINT SLEEVE FOR A PIPE COMPRISING AN INNER LINING

(71) Applicant: SAIPEM S.A., Montigny le Bretonneux (FR)

(72) Inventors: François Régis Pionetti, La Baleine (FR); François Lirola, Courbevoie (FR)

(73) Assignee: Saipem S.A., Montigny le Bretonneux (FR)

( * ) Notice: Subject to any disclaimer, the term of this patent is extended or adjusted under 35 U.S.C. 154(b) by 344 days.

(21) Appl. No.: 15/321,651

(22) PCT Filed: Jun. 29, 2015

(86) PCT No.: PCT/FR2015/051750
§ 371 (c)(1),
(2) Date: Dec. 22, 2016

(87) PCT Pub. No.: WO2016/001546
PCT Pub. Date: Jan. 7, 2016

(65) Prior Publication Data
US 2017/0210059 A1 Jul. 27, 2017

(30) Foreign Application Priority Data
Jul. 2, 2014 (FR) ..................................... 14 56299

(51) Int. Cl.
*B29C 33/48* (2006.01)
*B29C 65/34* (2006.01)
(Continued)

(52) U.S. Cl.
CPC ........ *B29C 65/342* (2013.01); *B29C 65/3432* (2013.01); *B29C 65/3468* (2013.01);
(Continued)

(58) Field of Classification Search
CPC ...... B29C 65/34; B29C 66/634; B29C 33/505
See application file for complete search history.

(56) References Cited

U.S. PATENT DOCUMENTS

| 2009/0078742 | A1* | 3/2009 | Pasquali | ............... | G01N 29/225 |
| | | | | | 228/103 |
| 2013/0114945 | A1* | 5/2013 | Pionetti | ..................... | F16L 1/15 |
| | | | | | 392/472 |

FOREIGN PATENT DOCUMENTS

| DE | 24 40 086 | 3/1976 |
| DE | 27 19 320 | 12/1978 |

(Continued)

OTHER PUBLICATIONS

Lirola, et al., "Fusion Bonded Joint: An Innovative Technology for Cost Efficient Plastic-Lined Pipe Installation and Operation", Deep Offshore Technology International Conference, Houston, Texas, 2015, 13 pages.

(Continued)

*Primary Examiner* — Scott W Doods
(74) *Attorney, Agent, or Firm* — Cozen O'Connor

(57) ABSTRACT

A device (20) for installing a tubular junction sleeve inside a pipe (1), having a mandrel (20*a*) of longitudinal axis (XX) supporting on its surface at least a first peripheral chamber (21) having a wall (21*a*) that is radially expandable by inflation. The first wall including at least one electrical connector (21*b*) suitable for being connected to one end of said heater wire. The connector being connected to an umbilical (24) including at least a compressed air feed duct for inflating the first chamber and an electrical power supply duct connected to the electrical connector. The device being characterized in that the mandrel supports on its outer surface a second peripheral chamber (22) having a wall (22*a*) that is radially expandable by inflation, and also a weld (Continued)

inspection device (23) arranged in the longitudinal direction of the mandrel.

14 Claims, 11 Drawing Sheets

(51) Int. Cl.

| | |
|---|---|
| *B29C 65/78* | (2006.01) |
| *B29C 65/82* | (2006.01) |
| *B29C 65/00* | (2006.01) |
| *F16L 58/18* | (2006.01) |
| *F16L 1/15* | (2006.01) |
| *F16L 1/20* | (2006.01) |
| *F16L 13/02* | (2006.01) |
| *F16L 47/03* | (2006.01) |
| *G01N 29/04* | (2006.01) |
| *G01N 29/22* | (2006.01) |
| *G01N 29/265* | (2006.01) |
| *B29C 65/48* | (2006.01) |
| *B29C 57/00* | (2006.01) |
| *B29K 705/00* | (2006.01) |
| *B29L 23/00* | (2006.01) |

(52) U.S. Cl.
CPC ...... *B29C 65/7838* (2013.01); *B29C 65/8253* (2013.01); *B29C 65/8292* (2013.01); *B29C 66/0016* (2013.01); *B29C 66/1142* (2013.01); *B29C 66/1162* (2013.01); *B29C 66/342* (2013.01); *B29C 66/5221* (2013.01); *B29C 66/53241* (2013.01); *B29C 66/612* (2013.01); *B29C 66/634* (2013.01); *B29C 66/72321* (2013.01); *B29C 66/73921* (2013.01); *F16L 1/15* (2013.01); *F16L 1/206* (2013.01); *F16L 13/0263* (2013.01); *F16L 47/03* (2013.01); *F16L 58/181* (2013.01); *G01N 29/043* (2013.01); *G01N 29/225* (2013.01); *G01N 29/265* (2013.01); *B29C 57/005* (2013.01); *B29C 65/48* (2013.01); *B29C 65/485* (2013.01); *B29C 66/1122* (2013.01); *B29C 66/636* (2013.01); *B29C 66/71* (2013.01); *B29K 2705/00* (2013.01); *B29L 2023/22* (2013.01); *G01N 2291/0289* (2013.01); *G01N 2291/267* (2013.01); *G01N 2291/2636* (2013.01)

(56) References Cited

FOREIGN PATENT DOCUMENTS

| | | |
|---|---|---|
| DE | 20 2011 101425 | 10/2012 |
| DE | 10 2011 103855 | 11/2012 |
| EP | 1 899 721 | 7/2005 |
| JP | H10 119135 | 5/1998 |
| WO | WO 01/71338 | 9/2001 |
| WO | WO 2006/042925 | 4/2006 |
| WO | WO 2010/041016 | 4/2010 |
| WO | WO 2012/017171 | 2/2012 |

OTHER PUBLICATIONS

Lirola, et al., "Fusion Bonded Joint: An Innovative Technology for Cost Efficient Plastic-Lined Pipe Installation and Operation-Qualification Campaign", Deep Offshore Technology International Conference, Houston, Texas, 2015, pages.

* cited by examiner

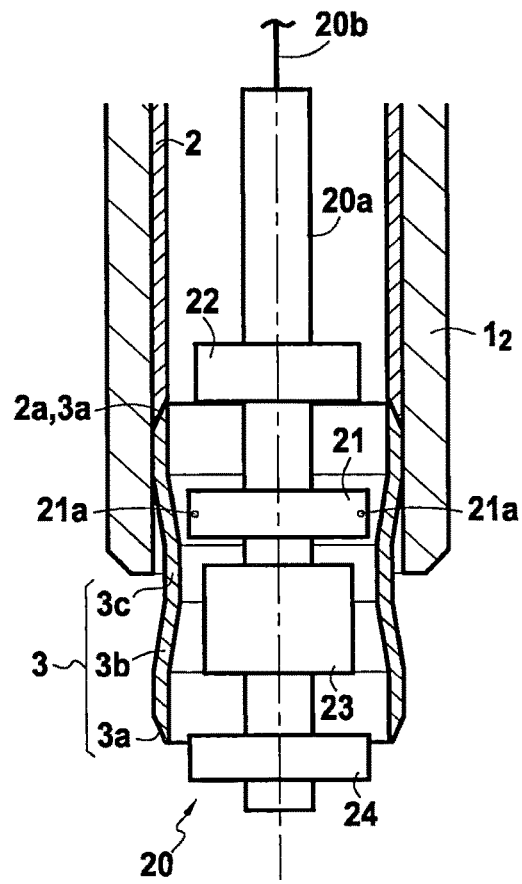
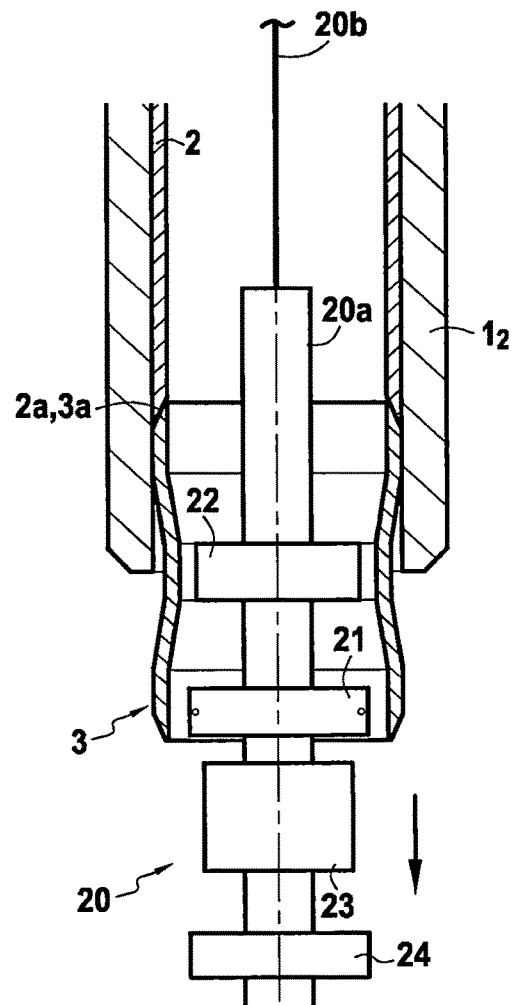
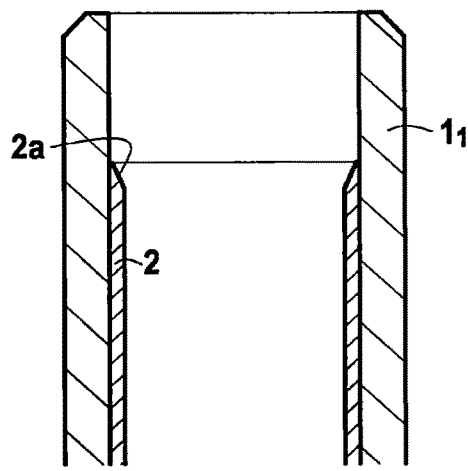
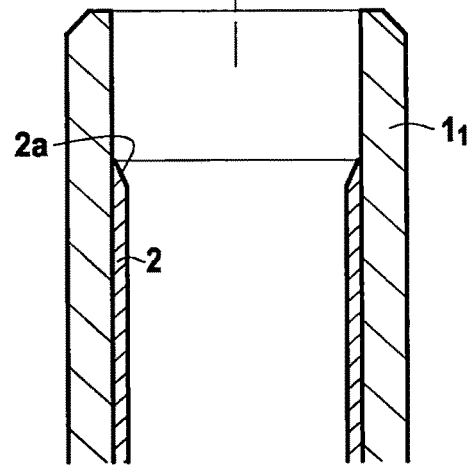
FIG.10  FIG.11

DEVICE AND METHOD FOR INSTALLING A TUBULAR JOINT SLEEVE FOR A PIPE COMPRISING AN INNER LINING

PRIORITY CLAIM

This is a U.S. National stage application No. PCT/FR2015/051750, filed on Jun. 29, 2015. Priority is claimed on France Application No.: FR1456299, filed Jul. 2, 2014, the content of which is incorporated here by reference.

BACKGROUND OF THE INVENTION

The present invention relates to the field of pipes made by assembling together steel pipe elements, each having an internal lining of plastics material protecting the steel walls of said pipe from corrosion.

The present invention relates more particularly to a device and a method for installing a tubular junction sleeve made of plastics material for assembling a pipe from said unitary pipe elements and for performing electro-fusion, said sleeve being pressed against and secured to said lining by electro-fusion by the Joule effect at the junction between the abutting ends of two unitary pipe elements, as described in particular in WO 2012/017171.

More particularly, the present invention relates to pipes for conveying corrosive fluids, in particular undersea pipes conveying sea water under pressure for injection into wells in oil fields, and still more particularly connection pipes resting on the sea bottom or bottom-to-surface connection pipes.

The present invention relates more particularly to connecting together two internally-lined unit pipe elements, and more particularly elements presenting a length of 24 meters (m) or 48 m that are installed in oil fields in deep water, e.g. in depths of 2000 m to 3000 m, or even more, from a laying ship fitted with J-lay towers.

In known manner, the ends of said pipe elements are assembled together end to end by welding, and the internal lining inside said pipe elements comes to an end at a significant distance from each end of said pipe elements, e.g. a distance of 100 millimeters (mm) to 300 mm, so that the heating of the steel wall while the ends are being welded together does not damage said lining. There is then a problem of how to protect against corrosion the non-lined zone extending between the end of the lining of pipe element No. N and the end of the lining in the following pipe element No. N+1.

Patent WO 2006/042925 in the name of the Applicant discloses such an assembly of pipes provided with internal linings. The internal lining method is known as "swagelining".

The terms "liner" or "internal lining" as used herein correspond to an internal covering commonly known as a "liner".

In WO 2012/017171, the Applicant describes an improved way of assembling together two pipe elements made of steel coated with internal lining by using a tubular junction sleeve, which method is both mechanically more reliable in terms of sealing while also being simple and inexpensive to perform, in particular when assembly is performed on site by a ship at sea, using pipe elements of short length that are suitable for laying from a ship at sea.

To do this, the tubular junction sleeve is interposed between two pipe elements made of steel with internal lining made of thermoplastic material that are assembled together end to end, the ends of the two pipe elements being welded together. Said tubular junction sleeve made of thermoplastic material, preferably of material identical to that of said lining, is inserted inside the pipe at the abutting ends of the two pipe elements, so that the terminal portions at the ends of said sleeve are at least partially in leaktight contact with respective terminal portions at the ends of said internal lining of the two pipe elements. Said tubular junction sleeve presents a Joule-effect heater wire at each of said terminal portions of the sleeve at said zone for leaktight contact with the terminal portions of said linings, which wire is on the outer surface of each of said terminal portions at the ends of said sleeve, and is preferably arranged as a spiral. Said zone of leaktight contact is a zone of welding by fusion between the materials constituting each said terminal portion of the sleeve and each said terminal portion of said lining where they come into with each other and where said heater wire passes.

It is important for the contact between the sleeve and the liner to be leaktight in order to avoid any sea water making contact with the welding zone facing said tubular sleeve. In the event of water penetrating between the sleeve and the pipe, and when the pipe is a water injection pipe, such direct contact could lead to electrochemical corrosion phenomena of the steel pipe and of the weld, assuming that said mechanical connection between the sleeve and the lining is not necessarily leaktight.

It can be understood that said fusion zone is obtained by electrically powering said Joule effect heater wire creating heating at the interface between said contacting surfaces of the terminal portions of the sleeve and of the lining. Said fusion-welding zone (referred to below as "fusion zone" for short) is thus performed in this example by the so-called "electro-fusion" method that makes it possible to provide a zone of leaktight contact that is particularly reliable and strong.

Said heater wire is applied on an outer surface of a terminal portion of the sleeve with one end of the heater wire reaching the inner surface of said sleeve at an electrical connector making it easier to electrically power the heater wire from inside the pipe while assembling the pipe, as explained below.

Said sleeve may be prefabricated with a said heater wire already applied to its surface, which is easier to perform than applying a heater wire in situ inside said pipe elements on the surfaces of said internal linings of the in situ pipe element inside the pipe before inserting said sleeve inside said pipe element.

In another implementation, the heater wire is not applied as a spiral, i.e. it is not made as a plurality of turns arranged in succession in the direction of their axis of revolution in order to cover said fusion zone, but said wire makes at least one turn around said axis of revolution around the fusion zone while performing a plurality of go-and-return paths between the two ends of said fusion zone in the axial direction of the axis of revolution of said fusion zone.

A method of making a pipe with such a sleeve comprises assembling together pipe elements, each including a said sleeve with a terminal portion of smaller thickness at each end, and a respective said tubular junction sleeve inserted into only one end of each said pipe element and projecting therefrom, the projection of said sleeve defining a male end of each said pipe element suitable for being connected to an end that does not have a said sleeve and that defines a female end of another said pipe element of the same kind. For this assembly, the following steps are performed:

1) said female end that does not have a tubular junction sleeve of a pipe element is then engaged by force around the male end of the stationary tubular junction sleeve that projects axially from the other pipe element in the longitudinal direction (XX') until said terminal portion of the sleeve of said male end of said terminal pipe element is in contact with said terminal portion of the lining of said female end of said pipe element for assembly, each said sleeve including on each of said terminal portions of the sleeve a said Joule effect heater wire wound in a double spiral; then 2) electrically powering said heater wire of said terminal portion, preferably while simultaneously exerting pressure between said contacting sleeve terminal portion and said lining terminal portion in order to provide a said zone for welding by electro-fusion in at least a portion of the interface at the surfaces of each said sleeve terminal portion and each said lining terminal portion in mutual contact and having the heater wire double spiral running thereover at the surface of the sleeve in order to provide a said zone of leaktight contact by fusion; and 3) welding together of the ends of the two abutting pipe elements at their outer peripheries.

In WO 2012/017171, said pressure is exerted against the inner surface of the sleeve via its said terminal portion by inserting inside the sleeve a device that includes an inflatable cell, which cell is initially deflated at least in part, said cell including or co-operating at its surface with an electrical power supply connector that is positioned in such a manner that, when said cell is inflated, said electrical connector of the cell can co-operate with the electrical connector on the inner surface of the sleeve including the terminals of the heater wire, and then said cell is inflated.

More precisely, in WO 2012/017171, and with reference to FIGS. 9A-9E, an expandable mandrel 20 is used that enables electro-fusion to be performed at the junction between the tubular sleeve 3 and the internal lining 2 via the surface of revolution 2a. The mandrel 20 has a rigid core 21 in the form of a wheel rim, an expandable membrane in the form of an air chamber 22 that can be inflated by means of an umbilical 23 fed with compressed air, said umbilical also delivering electrical power to a power supply connector 20a. The mandrel 20 is thus inserted inside the tubular junction sleeve 3 so as to position the connector 20a facing the complementary connector 7 of said tubular junction sleeve. The mandrel is then inflated and electricity is injected so as to melt said zone covered by the heater wire. Expansion of the mandrel serves to guarantee compactness in the fusion plane, and also to guarantee the absence of bubbles of air, where such bubbles would be harmful to good sealing in the melted surface.

Furthermore, said mandrel does not enable said junction sleeve to be inserted and installed prior to welding by electro-fusion, with the operations of installing the sleeve being difficult to perform.

SUMMARY OF THE INVENTION

Finally, it is found necessary to be able to inspect the quality of the welding performed by electro-fusion The object of the present invention is to overcome these problems and drawbacks and more generally to improve the device and the method for installing such a tubular junction sleeve made of plastics material in order to assemble in leaktight manner a pipe that includes an internal lining, said sleeve being pressed against and secured to said lining by electro-fusion by the Joule effect.

To do this, the present invention provides a device suitable for installing a tubular junction sleeve inside the end of a first pipe element made of steel and internally lined with a thermoplastic material, and suitable for butt-joining the end of the first pipe element fitted with a said sleeve and the end having no such sleeve of a second pipe element having internal lining of thermoplastic material, said ends of the two pipe elements abutting in this way being for welding together, said sleeve presenting at each end a terminal tubular wall portion, preferably of thickness that is smaller than the thickness of the adjacent running portion of the tubular wall of said sleeve, said sleeve presenting a Joule effect heater wire at at least one and preferably at both of said terminal portions of the sleeve, which Joule-effect heater wire(s) is/are arranged, preferably as a spiral, at the outer surface of said terminal portion of said sleeve suitable for creating by heating a zone of contact made leaktight by melting between the materials constituting at least a part of said terminal portion of the sleeve and respectively a terminal portion of said lining where they are in contact with each other with said heater wire running thereover, said device for installing a sleeve comprising a mandrel of longitudinal axis (XX') supporting on its surface at least a first inflatable chamber having a peripheral wall that is radially expandable by inflation, said first wall having at least one first electrical connector suitable for being connected to one end of a said heater wire, and said mandrel also supporting an umbilical including at least a compressed air feed duct for inflating said first inflatable chamber and an electrical power supply duct connected to said first electrical connector.

According to the invention, said mandrel also supports on its outer surface a second inflatable chamber having a peripheral wall that is radially expandable by inflation and that is spaced apart from said first inflatable chamber in said longitudinal direction, and said mandrel also supports a weld inspection device, said umbilical passing inside said mandrel and including ducts for electrically powering said weld inspection means, and preferably also for feeding them with water.

Preferably, said weld inspection device is arranged in the longitudinal direction of the mandrel upstream or downstream relative to said first and second chambers, preferably on the side of said first chamber other than the side on which said second chamber is located. In other words, said first chamber is arranged between said weld inspection device and said second chamber. The method of installing and using the sleeve with the device of the present invention are facilitated by the fact that said second chamber makes it possible:

to facilitate guidance and enable the device of the invention to be moved longitudinally more easily inside a pipe and/or a sleeve since said first and second chambers are partially inflated up to a diameter that is slightly smaller than the diameter of the pipe or the sleeve as the case may be, the two chambers being spaced apart in the longitudinal direction so as to come into abutment against the wall of the pipe and of the sleeve and thus hold the mandrel in the axial direction of the pipe or of the sleeve in spite of the opposing weight constituted by the weld inspection device; and to fasten the device of the invention inside said sleeve, thereby stabilizing the mandrel relative to said sleeve in order to adjust its position prior to performing said electro-fusion, by inflating said second inflatable chamber to its maximum extent so that it is pressed against the inside wall of the sleeve and secured thereto in spite of the opposite weight represented by the weld inspection means, position adjustment consisting in pre-positioning said first chamber facing said terminal sleeve portion for welding and connecting its electrical connector after inflating the first chamber; and to stabilize the device of the invention relative to said sleeve by inflating both of said first and second chambers to the maximum extent so that they are pressed against the inside wall of the sleeve and secured thereto while performing said electro-fusion and thereafter while using said weld inspection means in movement.

Preferably, said first and second inflatable chambers extend over respective lengths l1 and l2 and are spaced apart by a distance d in the longitudinal direction of the mandrel such that when a said first inflatable chamber is radially expanded to press against the terminal portion of the sleeve, in particular when the terminal portion is arranged against the terminal portion of the internal lining of the pipe in order to perform electro-fusion, the second inflatable chamber is in a facing position and can press against a portion of the tubular inside wall of said sleeve.

It can be understood that the position of the weld inspection device is then outside the sleeve. Furthermore, when said inspection means are placed facing a terminal electro-fusion portion, at least the first inflatable chamber, and preferably both the first and second inflatable chambers, in radial expansion can be pressed against the inside wall of the sleeve.

Preferably, said weld inspection device comprises:
at least one ultrasound probe; and
at least one water injection nozzle fed with water by a duct passing in said umbilical; and
preferably visual inspection means, preferably a camera.

The camera enables the device to be positioned in sight of the weld and enables the ultrasound weld inspection module to be properly placed in register with the weld for inspection and then to inspect the weld.

More particularly, said ultrasound probe and/or said water injection nozzle is/are suitable, after electro-fusion, for being turned facing the end portions of said sleeve about a turning axis arranged on the longitudinal axis of said mandrel said longitudinal axis. It can be understood that they are mounted on said mandrel in motor-driven manner to enable this to be done.

Devices are known for inspecting welding by an ultrasound probe. Such devices are constituted by a piezoelectric emitter made of ceramic material that emits an ultrasound wave for a short instant, which wave is transmitted through the mass of steel and metal of the pipe and the weld, and is reflected at the opposite surface of the pipe. In general, said emitter also acts as a receiver sensor, with the wave corresponding to the received wave being delivered by electronic processor means to a computer. In the context of inspecting a weld in plastic, the wave propagates and is reflected on any obstacle or defect it encounters. Obstacles include: the cables needed for delivering the power for electro-fusion, the plastic/plastic interface in the absence of welding, and the plastic/steel interface. The stronger the echo at the interface between plastic and steel, the greater the quality of the weld.

Ultrasound probes are also known that comprise a series of emitter-receivers and that are referred to as "phased-array" or multibeam probes. The operating structure is described in EP 1 899 721, in particular so as to improve inspection of the weld, the various emitters emitting waves in different directions, thereby enabling the geographical zone that is inspected to be extended.

Such devices are generally operated manually by an operator and they are moved over and close to the weld, both axially in front-to-rear translation over the weld zone, and all around the circumference of the periphery of the pipe in said weld zone, as described in WO 01/71338.

When working from the inside of the pipe, an operator finds it very difficult to position the ultrasound probe accurately by hand, not only because of the distance of the weld zone for inspection from the end of the pipe, but also because of the difficulty of viewing correctly the exact position of the weld that is to be inspected, thus making it very difficult to show up critical defects in the weld. The problem is made worse when the diameter of the inner pipe is small. Furthermore, when the operator identifies a defect, the exact position of said defect is not known with great accuracy, specifically because the operation is performed manually. In EP 1 899 721, an independent motor-driven carriage is used that is moved inside the pipe.

Preferably, said mandrel also supports reversible shutter means for shutting the passage between the mandrel and the inside wall of the sleeve or of the pipe, said shutter means being arranged in said longitudinal direction of the mandrel so that said weld inspection means are arranged between said shutter means and at least one said first or second chamber.

It can be understood that said reversible shutter means can thus be used either to close the passage between the mandrel and the inside wall of the sleeve when the portion of the mandrel supporting said shutter means is positioned inside said sleeve; or else to close the passage between the mandrel and the pipe when the portion of the mandrel supporting said shutter means is positioned inside the pipe. The shutter means are said to be "reversible" in that they can be actuated to close the passage as described above and that they can be actuated reversibly to re-open said passage and enable the device of the invention to be moved longitudinally.

More particularly, said reversible shutter means are constituted by a third inflatable chamber having a peripheral wall that is radially expandable by inflation.

Still more particularly, said expandable wall of said second inflatable chamber includes at least one electrical connector suitable for being connected to the end of a said heater wire.

It can be understood that:
said first and second inflatable chambers are arranged in annular or toroidal manner around the cylindrical mandrel or around a rigid core forming a wheel rim around the mandrel; and
said electrical connectors are connected to or suitable for being connected to an electrical power supply duct contained in said umbilical and passing through one or both of said first and second inflatable chambers containing it, and said inflatable chambers are also connected to compressed air feed ducts contained in said umbilical.

In a particular embodiment, each of said inflatable chambers is formed by a flexile or semi-rigid tubular envelope of circular cross-section arranged around said cylindrical mandrel, and about the same longitudinal axis XX' as said mandrel, the circular edges of each longitudinal end of each said envelope joining the outer wall of said mandrel in such a manner that under the effect of said chamber being inflated said envelope takes on a convex bulging shape in axial longitudinal section forming the radially expanded wall of said chamber.

The present invention also provides a method of installing a tubular junction sleeve at one end of a unitary pipe element having an internal lining made of thermoplastic material in order to fasten a said sleeve to the terminal portion of a said lining, said sleeve presenting at each end a terminal portion of tubular wall that is preferably of thickness that is smaller than the thickness of the adjacent running portion of the tubular wall of said sleeve, said sleeve presenting a Joule-effect heater wire at at least one, and preferably at each, of said terminal portions of the sleeve, which Joule-effect heater wire is arranged, preferably as a spiral, at the outer surface of said terminal portion of said sleeve, and heating is used to create a leaktight contact zone by melting together materials constituting at least fractions respectively of said terminal portion of the sleeve and of a terminal portion of said lining that are in contact with each other, with said heater wire passing therethrough, by using a device of the invention for installing a sleeve.

More particularly, the following steps are performed, preferably on the deck of a ship or on land:

i.1) positioning said device for installing a sleeve inside said sleeve in such a manner that at least a said first inflatable chamber is in position facing a first terminal portion of the sleeve with its first connector facing an end of said heater wire, the other one of said first and second inflatable chambers facing the inside wall of the running portion of the sleeve, and inflating at least said second inflatable chamber so as to secure the device for installing a sleeve with said sleeve by pressing the expandable wall of said second chamber against the inside wall of said tubular sleeve; and i.2) moving the resulting assembly of the sleeve and said device for installing a sleeve axially in the longitudinal direction (XX') and inserting it inside a sleeve-free open end of a pipe element until said first terminal portion of the sleeve is in contact with said terminal portion of the lining of said female end of said pipe element; and i.3) inflating said first inflatable chamber to press it against the inside wall of said first terminal portion of the sleeve so that said first electrical connector is connected to one end of a said heater wire, preferably by means of a complementary electrical connector; and i.4) electrically powering said heater wire while simultaneously exerting pressure from said terminal sleeve portion against said terminal lining portion that are in contact with each other by inflating said first inflatable chamber in order to implement a said weld zone by electro-fusion of the materials constituting at least fractions respectively of said terminal portion of the sleeve and of a terminal portion of said lining that are in contact with each other, with said heater wire passing therebetween; and i.5) deflating said first and second inflatable chambers and moving said device for installing a sleeve in translation in such a manner that said weld inspection device is placed facing said terminal sleeve portion corresponding to said zone of welding by electro-fusion; and i.6) once more inflating the first and second inflatable chambers so that they press against the inside wall of the sleeve and become secured thereto, and actuating said weld inspection device to inspect said weld, preferably by injecting water against said terminal portion of the sleeve;

i.7) deflating said first and second chambers and moving said device for installing a sleeve in translation in order to remove it.

It can be understood that said pipe element that is obtained has a sleeve portion beside the free second terminal portion outside the corresponding pipe element at said male end of step a) of the following pipe-making method.

At step i.6), water serves to provide better transmission of ultrasound waves to the plastic for inspection.

The present invention also provides a method of making a pipe using a device of the invention for installing a sleeve, wherein by assembling unitary pipe elements, each including a said lining, preferably with a terminal portion of smaller thickness at each end, with a said tubular junction sleeve inserted and fastened to only one end of each said pipe element and projecting therefrom, the projecting part of said sleeve defining a male end of each said pipe element suitable for being assembled with a sleeve-free end defining a female end of another said pipe element, said sleeve presenting at each of its ends a terminal tubular wall portion that is preferably of thickness that is smaller than the thickness of the adjacent running portion of the tubular wall of said sleeve, said sleeve presenting a Joule-effect heater wire at at least one, and preferably at each, of said terminal portions of the sleeve, which Joule-effect heater wire is arranged, preferably in a spiral, at the outer surface of said terminal portion of said sleeve suitable for creating, by heating, a contact zone made leaktight by melting together the materials constituting at least fractions respectively of said terminal portion of the sleeve and of a terminal portion of said lining that are in contact with each other, with said heater wire passing therebetween, by performing the following steps:

a) inserting a device for installing a sleeve inside a said unitary pipe element so that said first inflatable chamber is arranged with its first electrical connector facing the end of a heater wire at a terminal portion of said sleeve that is fastened thereto, and fastening said device for installing a sleeve inside said sleeve by inflating a said second inflatable chamber against the inside wall of said sleeve; and b) before or after step a) forcibly inserting the sleeve portion forming said male end of a pipe element in the female end of the other pipe element axially in the longitudinal direction (XX') until said terminal portion of the sleeve of said male end of said terminal pipe element comes into contact with said terminal portion of the lining of said female and of said pipe element to be assembled therewith; and c) welding together of the ends of the two abutting pipe elements at their outer peripheries; and d) inflating a said first inflatable chamber and connecting its said first electrical connector to the end of the heater wire at said terminal portion of the sleeve and facing it, and electrically powering said heater wire, while simultaneously exerting pressure from said terminal portion of the sleeve against said terminal portion of the lining that are in contact with each other in order to make a said weld zone by electro-fusion in at least a fraction of the interface between the surfaces of each said terminal portion of the sleeve and each said terminal portion of lining that are in contact with each other with the heater wire passing therebetween at the surface of the sleeve in order to make a said contact zone that is made leaktight by melting; and e) deflating said first and second inflatable chambers and moving said device for installing a sleeve in translation.

More particularly, the following steps are performed:

a.1) using a pipe-laying tower of a laying ship to lower a first pipe element fitted with a said sleeve at one of its ends to the proximity of the end of the top terminal pipe element of the pipe that is being assembled and that is partially immersed at the bottom of the tower; and a.2) lowering a said device for installing a sleeve (20) with said first and second chambers at least partially deflated, which device is secured to a said sleeve fastened to one of said first or second pipe elements by inflating a said second chamber that is pressed against the inside wall of the sleeve in its running portion, said first chamber being placed facing a free terminal portion of said sleeve with its first connector facing one end of said heater wire;

a.3) inflating the first chamber that presses against the terminal portion of said sleeve so that said electrical connector is connected to one end of said heater wire, preferably via a complementary electrical connector; and b) after or before step a.3) assembling together the two pipe elements by forcibly inserting the portion of a sleeve forming a said male end of one pipe element into the sleeve-free female end of the other pipe element;

c) butt-welding the ends of the two pipe elements together; and d.1) electrically powering said heater wire while simultaneously exerting pressure from said terminal sleeve portion against said terminal lining portion that are in contact with each other by inflating said first chamber in order to make a said weld zone by electro-fusion; and d.2) deflating said first and second chambers, and moving said mandrel so that said weld inspection means are placed facing said electro-welded terminal sleeve portion; and d.3) inflating the first and second chambers so that they press against the inside wall of the sleeve and are secured thereto; and d.4) actuating said weld inspection means in order to inspect said weld, preferably simultaneously injecting water against said terminal portion of the sleeve.

Still more particularly, in step d.4), the following steps are performed:

d.4.1) actuating said shutter means to close so as to form a leaktight compartment defined by said first inflatable chamber and said shutter means closing the passage inside the pipe, said leaktight compartment containing said weld inspection means for inspecting said weld; and d.4.2) filling said leaktight compartment with water and actuating said weld inspection means in order to inspect said weld; and d.4.3) thereafter, actuating said reversible shutter means to open them.

Still more particularly, before step a), steps i.1) to i.7) of the method of installing a tubular junction sleeve are performed at one end of a unitary pipe element of the invention, preferably on the deck of the ship or on land, in order to fasten a said sleeve to the terminal portion of one pipe element before it is assembled with another said pipe element.

The terms "inner" and "outer" are used herein respectively to designate inside and outside the pipe, the sleeve, or the lining, as appropriate.

The term "running portion of the sleeve" is used herein to mean the central portion of the sleeve situated between the two terminal portions at the two longitudinal ends of the sleeve.

As explained below, said terminal portions of the sleeve and of the lining may be in mutual contact via outer surfaces of revolution of said terminal portions of the sleeve coming into contact with inner surfaces of revolution of said linings, or via plane annular surfaces at the frontal ends of right section of said terminal portions of the sleeve and of said lining. Said surfaces of revolution of said terminal portions of the sleeve and of the lining present the same axis of revolution as said pipe.

Said zone of leaktight contact extends all around the mutually-contacting outer surfaces of revolution of said terminal portions of the sleeve and inner surfaces of revolution of said terminal portions of the lining, i.e. over 360° around their axis of revolution XX'. In contrast, said zone of leaktight contact may extend over only a fraction of the lengths in the axial direction of said surfaces of revolution of the terminal portions of the sleeve and of the lining that are in mutual contact.

It can be understood that said surfaces of revolution of said terminal portions of the sleeve and of the lining present the same axis of revolution as said pipe and as said sleeve when in position inside said pipe.

In known manner, each said pipe element has an internal lining made of plastics material, preferably of thermoplastic material, that terminates at a certain distance l from the end of said pipe element, and preferably at least a fraction of the outer surface of each terminal portion at the ends of said internal lining being suitable for being held by adhesive against the corresponding inner surface of the steel wall of the pipe using an adhesive that is preferably of the epoxy or polyurethane type.

Also in known manner, the sleeve extends in a longitudinal axial direction XX' of the pipe over a length covering at least the lengths of pipe that are not covered by said linings, i.e. at least twice said distance l.

It can be understood that the outer surface of the running portion of the sleeve adjacent to said terminal portion of the sleeve is situated facing portions of the inner walls at the ends of said assembled-together pipe elements that are not covered by said lining.

It can be understood that the terminal portions at the ends of the sleeve present surfaces of shapes that are identical or complementary to the surfaces of the terminal portions at the ends of said linings with which they are in contact.

In a first variant implementation, the wall of the sleeve at at least one of said terminal portions of the sleeve is of substantially the same thickness as the thickness of the adjacent running portion of the sleeve facing the non-lined pipe, and of substantially the same thickness as the thickness of a said terminal portion of said lining and as the thickness of the adjacent running portion of said lining, said fusion-welding zone being situated at the right frontal ends of the sleeve and of said lining in abutment against each other.

It can be understood that said right frontal ends form annular plane surfaces extending in a direction perpendicular to the longitudinal direction XX' of the sleeve and of the pipe and that they are constituted by the edge faces in right cross-section of said ends.

In this implementation, the spiral formed by the heater wire is plane and it progresses around said frontal surface or edge face at the end of the sleeve in such a manner that the diameters of its concentric turns that are all situated in the same plane increase going from said first end that is closest to the inner surface of the sleeve towards its said second end that is closest to the adjacent outer surface of the sleeve situated facing the inner wall of the pipe.

In a second variant implementation that is more particularly advantageous for small thicknesses, in particular thicknesses of less than 10 mm, said internal lining presents, at at least one end, a terminal portion of thickness that is smaller than the thickness of the running portion of said lining, defining a concave shape with an inner surface of revolution of inside diameter that is greater than the inside diameter of the running portion of said lining, and said sleeve presents, at at least one end, a terminal portion of thickness that is smaller than the thickness of the adjacent running portion of said sleeve, said terminal portion of the sleeve defining a convex shape suitable for extending over the concave terminal portion of smaller thickness of said lining with which it is in contact, said terminal portion of the sleeve defining an outer surface of revolution of outside diameter that is less than the outside diameter of the adjacent running portion of the sleeve and a cylindrical inner surface of substantially the same inside diameter as the inside diameter of said running portion of the lining and of said running portion of the sleeve, said Joule-effect heater wire running over the entire periphery of said outer surface of revolution around its axis of revolution (XX') and over at least a fraction of the length of said terminal portion in the direction of said axis of revolution (XX').

By virtue of their complementary shapes, it can be understood that said terminal portion of the sleeve and said terminal portion of smaller thickness of the lining enable the sleeve to be inserted against the inner surface of the terminal portion of smaller thickness of the lining merely by engaging said sleeve by force in the axial longitudinal direction XX' inside said pipe element, and the outer surface of said terminal portion of smaller thickness of the sleeve in contact with the inner surface of the terminal portion of smaller thickness of the lining present identical shapes and are arranged relative to each other so that their identical outlines match.

In a first sub-variant of the second variant, said inner surface of the smaller-thickness terminal portion of the lining and said outer surface of the smaller-thickness terminal portion of the sleeve covered in said heater wire that are in contact with each other have the same frustoconical shape about the common axis XX' of said sleeve and said pipe.

It can be understood that by their respective complementary concave and convex shapes, said frustoconical inner and outer surfaces present respective angles at the apex of substantially the same value. In this implementation with a frustoconical contact surface, said smaller-thickness terminal portions of the sleeve and of the lining that are in contact present a thickness that increases going from the ends of the sleeve and the lining respectively towards the adjacent running portions of the sleeve and of the lining respectively, and the spiral of the heater wire advances with turns of increasing diameter from its said first end situated beside the smaller-thickness terminal portion of the sleeve towards its said second end situated beside the greater-thickness terminal portion of the sleeve.

In a second sub-variant of this second variant, said inner surface of the smaller-thickness terminal portion of the lining and said outer surface of the smaller-thickness terminal portion of the sleeve that are in contact with each other have the same cylindrical shape about the common axis XX' of said sleeve and said pipe, and preferably the end of the smaller-thickness terminal portion of the sleeve that is covered in said heater wire comes into abutment against a shoulder defining the inner surfaces of said running portion and of said smaller-thickness terminal portion of the lining.

In this embodiment with a cylindrical contact surface, said contacting smaller-thickness terminal portions of the sleeve and of the lining present respective thicknesses that are preferably identical and substantially constant, and the double spiral of the heater wire progresses with turns of constant diameter from its said first end situated beside the smaller-thickness terminal portion of the sleeve towards its said second end situated beside the greater-thickness terminal portion of the sleeve.

When the inner surface of the smaller-thickness terminal portion of the sleeve is conical or cylindrical, the double spiral formed by the heater wire is three-dimensional, i.e. of a helical shape since its turns are spaced apart in the longitudinal direction of the sleeve.

In the various above-described implementations having contacting surfaces of the terminal portions of the sleeve and of the liner that are frontal, conical, or spherical, the contact surface presents a topology of the cone type with the half angle at the apex a lying between 0° and 90° for surfaces that are conical, and of the type having a fictitious cone with a half angle at the apex $\alpha=90°$ for frontal ends of right section, and $\alpha=0°$ for surfaces that are so little, such that in all circumstances said first end of the spiral is situated beside the apex of the cone or of the fictitious cone. Preferably, as described in WO 2012/017171, a heater wire wound in a double spiral as defined above is used with the two free (non-spiral-wound) ends of the wire being situated on the same side of the double spiral so as to be able to reach the inner surface of the sleeve as close as possible to said inner surface. Thus, when the wire is used on an outer surface of revolution, it is possible to use a heater wire having its two free ends situated on the same side of the electro-fusion zone, i.e. the side remote from said metal weld. Thus, a fluid under pressure cannot access said metal weld by passing through the thickness of the sleeve to the fusion zone, but can only pass in the interface between the leaktight contact zone or fusion zone and the inside of the pipe.

The implementation with a heater wire wound in a double spiral is advantageous in that it makes it possible to ensure sealing that is more complete and more reliable for the contact surface between said terminal portions of the sleeve and of the lining so as to avoid any risk of said weld coming into contact with water when said pipe conveys water and thus avoid any risk of the zone situated between the outer surface of the sleeve and the inner surface of said pipe elements being invaded, which would inevitably constrict the inside diameter of the sleeve, i.e. reduce its section for passing fluid flow, thereby giving rise to disturbances in the flow of fluid inside the sleeve, without mentioning the risk of said weld coming into contact with water, when said pipe is used to convey water.

Because the two non-spiral-wound free ends of the wire start from the same end of the double spiral beside the non-leaktight portion of the interface leading solely to the inner surface of the sleeve, a fluid under pressure cannot pass through the thickness of the sleeve to the second end and therefore cannot gain access to said weld, but can only pass into the interface and into the channels for the ends of the wire between said first ends of the double spiral and the inside of the pipe.

More particularly, the pipe that is to be made is a connection pipe, either a pipe resting on the sea bottom, or a bottom-to-surface connection pipe suitable for being laid in sea of great depth, preferably up to 3000 m, and said pipe elements present a length lying in the range 20 m to 50 m, of inside diameter lying in the range 10 centimeters (cm) to 60 cm, and said sleeve presents a length lying in the range 45 cm to 150 cm. More particularly, the pipe is a pipe for injecting water under pressure into wells in an oilfield, which pressure is always greater than 5 megapascals (MPa) and more particularly lies in the range 25 MPa to 70 MPa (250 bars to 700 bars). As mentioned above, this type of pipe is particularly stressed at said welds, so they need to be protected as much as possible against any corrosion due to contact with seawater, in particular for bottom-to-surface connections since under such circumstances the pipe is perpetually in movement as a result of the effects of swell, wind, and current acting on the floating support at the surface, thereby subjecting the pipe to extreme levels of fatigue stress. Furthermore, the properties of the fluid being conveyed can make it necessary to include large extra thickness of sacrificial steel, thereby having a major impact on the installation of such pipes. Installing a lining made of plastic enables this need to be eliminated.

In another embodiment, said sleeve is made by assembling together by fusion welding, preferably by electro-fusion, surfaces at the mutually-contacting ends of at least two tubular portions of said sleeve comprising at least:

a first tubular sleeve portion having a running sleeve portion and a central sleeve portion, the central sleeve portion being of outside diameter and preferably also of inside diameter that are of dimension(s) smaller than the outside diameter, and preferably also respectively the inside diameter, of the adjacent running portion, more preferably said first tubular sleeve portion being obtained by machining a tubular sleeve of greater thickness; and at least one second tubular sleeve portion having a terminal tubular sleeve portion preferably presenting a length that is shorter than said first tubular portion in the axial direction XX' of the sleeve, and preferably presenting a cylindrical inner surface, and more preferably said second sleeve portion being obtained by molding; and the ends of said first and second assembled together tubular sleeve portions presenting shapes that are identical or complementary in their contact zone, with at least one of said surfaces being covered by a said Joule effect heater and having its end terminals more preferably leading to the inner surface of said tubular sleeve portion.

This implementation comprising a plurality of tubular sleeve portions makes it possible to limit the provision of molded parts to parts that are of relatively small size, thereby avoiding any need to use molds of large size, which are very expensive.

As with the terminal portions of the sleeve and of the lining, said complementary concave and convex shapes of the two tubular sleeve portions that are assembled together by electro-fusion may present identical surfaces having shapes that are:

conical, or cylindrical for the ends of said smaller-thickness tubular sleeve portions; or plane annular surfaces, said to be "frontal" surfaces, the tubular sleeve portions being assembled together via their edge faces that lie in a plane perpendicular to said longitudinal direction XX' of the sleeve.

Said sleeve may be constituted by assembling together by electro-fusion welding a said first tubular sleeve portion that is assembled to each end of a said second tubular sleeve portion, each said second tubular sleeve portion having a free end including a said terminal sleeve portion.

In an implementation in which assembly is mechanically particularly reliable, said first and second tubular sleeve portions present, at their assembled-together ends, respective concave and convex complementary shapes, the conical inner surface of said first tubular sleeve portion or said conical outer surface of said second tubular sleeve portion being covered in a said spiral-wound heater wire. This implementation is more particularly advantageous, and for performing said assembly by electro-fusion of said first and second tubular end portions in situ by initially inserting said second tubular sleeve portion that is assembled by electro-fusion with a terminal portion of an internal lining of a pipe element, and then assembling said first tubular sleeve portion and said second tubular sleeve portion with each other. Under such circumstances, the chamfered end for assembly of said first tubular sleeve portion engages like a wedge in the sharp angular gap, with the concave conical inner surface wedged in abutment against the conical convex outer surface of the end of said second tubular sleeve portion.

Preferably, in a central portion, said sleeve presents an outside diameter that is less than the outside diameters of the running portions adjacent to said central portion so as to leave an annular space between the sleeve and the wall of said pipe elements, and, if necessary, an annular thermal protection part is placed therein suitable for protecting the sleeve while the ends of the pipe elements are being welded together, said running portions of the sleeve preferably presenting an outside diameter that is substantially identical to the inside diameter of the ends of the assembled-together pipe elements that are not covered by said lining.

This implementation is particularly advantageous in that it makes it possible to create an annular gap of sufficient size for receiving a said annular part for thermally protecting the sleeve, thereby preventing the sleeve being damaged while welding together the steel ends of said pipe elements for assembly, thereby protecting the outer surface of the sleeve facing said ends of the pipe elements that are to be welded together.

Also preferably, the tubular wall of said sleeve presents thickness that is substantially constant in its said adjacent running portions and substantially equal to the thickness of the running portion of said internal lining, and said central portion of the sleeve, which is preferably of smaller thickness, is suitable for deforming so as to adopt an inside diameter that is substantially identical to the inside diameter of the remainder of the sleeve under the effect of an internal pressure of at least 1 MPa of the fluid that flows inside the pipe in operation, and the thermal protection part is itself also deformable under the same pressure conditions preferably so as to adopt a thickness of less than 5 mm, and more preferably of less than 2 mm, said thermal protection part more preferably being constituted by ceramic fibers.

Methods of making internal lining elements for pipe elements, and methods of assembling pipe elements including internal lining with the help of a tubular sleeve are described in WO 2006/042925, and can be applied in the present invention; in particular it is possible to make the internal lining using a method comprising the following steps:

1) inserting, via a first end of a pipe element, a pipe made of flexible and elastic thermoplastic material and in the shape of a pipe of circular section or of section folded into the shape of a kidney bean, in order to constitute said liner, and pulling it inside said pipe element up to the second end of the pipe element, and then releasing traction so as to enable it to expand radially and press against the inner surface of the wall of said pipe element; and 2) cutting and machining the ends of said lining pipe so as to form said terminal portions of smaller thickness of said internal liner and a non-lined terminal portion of the steel wall of said pipe element at each of its two ends.

BRIEF DESCRIPTION OF THE DRAWINGS

Other characteristics and advantages of the present invention appear in the light of the following detailed description with reference to the following figures, in which:

FIGS. 10 to 21 show various steps of assembling together two pipe elements with the sleeve 3 being installed and welded at one end of a first pipe element at the level of the sleeve-free end of a second pipe element and using a device of the present invention, which device is shown diagrammatically.

DETAILED DESCRIPTION OF THE PRESENTLY PREFERRED EMBODIMENTS

Figure 1A:
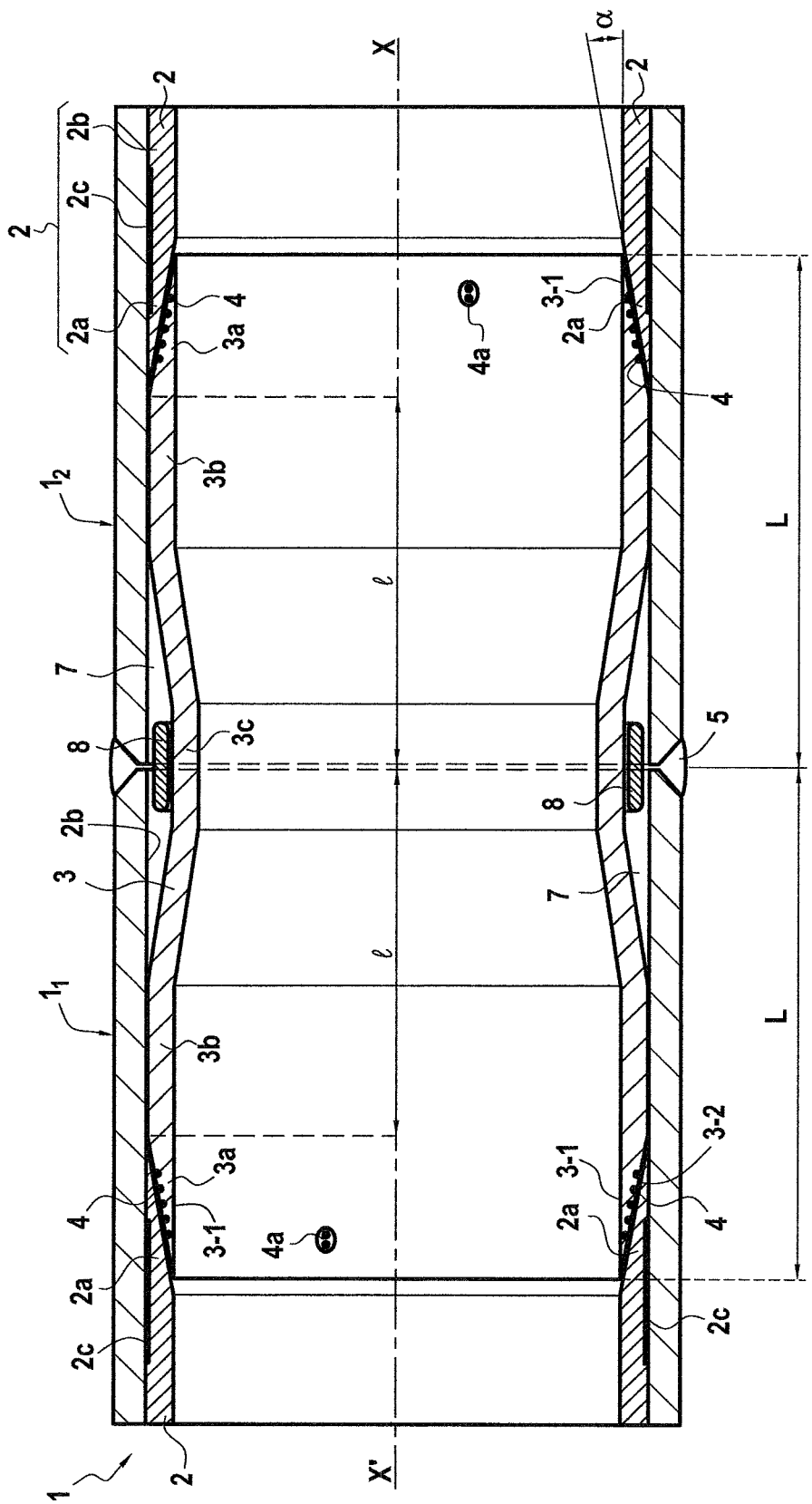
FIG. 1A is a side view in section of a pipe of the invention assembled with the help of a tubular junction sleeve between two lined pipe elements or unit pipe lengths of the invention.

FIG. 1A shows a pipe 1 of the invention comprising at least two pipe elements $1_1$ and $1_2$ with internal lining 2 of polyethylene or polypropylene, the elements being assembled together end to end, and the ends of the two pipe elements being joined together by a weld 5. Each pipe element has an internal lining of thermoplastic material 2 of axis XX' that coincides substantially with the axis of the pipe elements $1_1$, $1_2$, the linings presenting at each end respective conical terminal portions 2a of half-angle at the apex α that are of thickness that is smaller than the thickness of the running portion 2b of said lining, thereby defining an internal surface of revolution of inside diameter that is greater than the inside diameter of the running portion 2b of said lining and terminating at a certain distance L from each end of said pipe element. The outer surface of each of said terminal portions 2a of smaller thickness of the inner liner is optionally locked by adhesive bonding 2c of the end of the liner at or near said terminal portion of smaller thickness 2a of the liner against the corresponding inner surface of the steel wall of the pipe, using an adhesive that is preferably of the polyurethane or the two-component epoxy type.

A tubular junction sleeve 3 of thermoplastic material, preferably identical to the thermoplastic material of the internal lining 2, and of axis XX' coinciding substantially with the axis of the pipe elements $1_1$, $1_2$ of the same outside diameter that is slightly smaller than the inside diameter of the pipe is inserted inside each of the abutting ends of the two pipe elements so as to extend over said terminal portions of the two linings 2a, 2b, by means of a device 20 of the invention as described below with reference to FIGS. 1 to 9.

More precisely, in FIG. 1A, the internal lining 2 presents at each end of a pipe element a terminal portion 2a of thickness that is smaller than the thickness of the running portion 2b of said lining so as to define a concave shape with a frustoconical inner surface with a half-angle at the apex α, of inside diameter that is greater than the inside diameter of the running portion 2c of said lining, and said sleeve 3 presents, at each of its longitudinal ends, a terminal portion 3a of thickness that is smaller than the thickness of the adjacent running portion 3b of said sleeve, said terminal portion 3a of the sleeve defining a convex shape suitable for extending over the smaller-thickness terminal portion of said lining 2a with which it is in contact, said terminal portion 3a of the sleeve defining a frustoconical outer surface 3-2 of outside diameter that is smaller than the outside diameter of the adjacent running portion 3b of the sleeve, and having the same angle at the apex α as said frustoconical inner surface of said concave terminal portion of said lining. The conically-shaped terminal portions of the sleeve define a cylindrical inner surface 3-1 having substantially the same inside diameter as said running portion 2b of the lining and as said running portion 3b of the sleeve.

In FIG. 1A, the sleeve presents a central portion 3c, i.e. about halfway along the sleeve in its axial longitudinal direction XX', with an outside diameter that is smaller than the outside diameters of the running portions 3b adjacent to said central portion 3c so as to leave an annular space 7, and an annular thermal protection part 8 is placed therein for protecting the sleeve while welding together the ends of the pipe elements, said running portions 3b of the sleeve presenting an outside diameter that is substantially identical to the inside diameter of the uncovered ends of said lining of the assembled-together pipe elements.

The tubular wall of said sleeve presents thickness that is substantially constant in its central portion 3c and its adjacent running portions 3b, which thickness is substantially equal to the thickness of the running portion 2b of said internal lining 2, and said central portion 3c of the sleeve is suitable for deforming so as to adopt an inside diameter that is substantially identical to the inside diameter of the remainder of the sleeve under the effect of internal pressure from a fluid flowing inside the pipe in operation, which pressure is at least 1 MPa, and the thermal protection part 8 is itself also deformable under the same conditions of internal pressure inside the pipe so as to adopt a small thickness, preferably a thickness of less than 5 mm and more preferably less than 2 mm, said thermal protection piece more preferably being constituted by ceramic fibers in a form similar to cotton wool.

It can be understood that:

because of its substantially constant thickness, the central portion of the sleeve presents a constriction in outside diameter and in inside diameter during laying with the pipe being empty and at atmospheric pressure or when it is subjected to pressures corresponding to pressure values of less than 1 MPa (10 bars); and as soon as the inside pressure exceeds 1 MPa (10 bars), the thicknesses, in particular of about 5 mm to 20 mm, and the stiffness of the plastics material, such as polyethylene or polypropylene, enable the inside and outside diameters of the central portion to be increased by deformation, e.g. when a fluid, in particular water under pressure, flows inside the pipe and the sleeve, as occurs in water injection pipes for oil wells at a pressure greater than 5 MPa, and in particular lying in the range 25 MPa to 70 MPa.

Because the pressure $P_0$ outside the lining is much less than the internal pressure Pmax, this pressure has the effect of firmly pressing the constricted central portion 3c of the tubular junction sleeve 3 against the wall of the steel pipe, the ceramic fiber shield 8 being likewise flattened and then presenting a residual thickness of no more than 1 mm to 2 mm.

The sleeve 3 presents a central portion 3c of constricted outside diameter that becomes pressed against the inside of the pipe as soon as the internal pressure exceeds 1 MPa to 1.5 MPa (10 bars to 15 bars) because of the flexibility of the thermoplastic material. To improve the deformability of this central portion 3c and of the adjacent transition zones, the thickness of these zones is advantageously smaller than the thickness of the running portion 3b of the sleeve by a proportion lying in the range 5% to 50%. Likewise, the central zone 3c and the transition zones, which are shown for clarity in the drawings of having sharply angled connections, are preferably connection fillets of large radius of curvature so as to avoid incipient cracks appearing in these zones.

FIG. 1A shows a heater wire 4 forming a spiral, preferably a double spiral made up of two wire portions arranged side by side, forming two substantially equidistant spirals that are joined at a common end constituted by a hairpin-bend like those described in WO 2012/017171. Each spiral travels along said outer surface 3-2 of each said terminal portion of the sleeve. The two free ends of the wire have respective electrical power supply terminals connected side by side at a common electrical connector 4a on the inner surface 3-1 of the sleeve.

FIGS. 1 to 9 show the various steps of installing a tubular junction sleeve 3 at one end of a pipe element $1_1$ using a device 20 for installing the sleeve. These operations may be performed on land or on the deck of the ship in a horizontal position A device 20 of the invention for installing a sleeve 3 as shown in FIGS. 1 to 9 is provided with a mandrel 20a of cylindrical shape extending in an axial longitudinal direction XX' and having a longitudinal cylindrical central orifice within which there is placed an umbilical 20b that also serves as a cord for handling the device 20.

In FIGS. 1 to 21, the device 20 has a first inflatable chamber 21 fitted with electrical connectors 21a arranged in the longitudinal direction XX' at a distance d from a second inflatable chamber 22. The first chamber 21 is interposed in the longitudinal direction between firstly the second chamber 22 and secondly the weld inspection device 23 that is also supported by the mandrel 20a. The mandrel 20a also supports a third inflatable chamber forming an extendible wall 24 arranged in the direction XX' so that the weld inspection means 23 are interposed between the first inflatable chamber 21 and the third inflatable chamber 24.

The first and second chambers are spaced apart by a distance d such that when the second chamber 22 faces the constricted central portion 3c of the sleeve, the first chamber 21 faces one end of the sleeve at its terminal portion 3a of smaller thickness. The weld inspection device 23 is then situated outside the sleeve. The weld inspection device 23 is arranged in the longitudinal direction such that when the second chamber 22 is placed facing the opposite end of the sleeve, as shown in FIG. 6, the weld inspection device 23 faces the first end of the sleeve and is thus suitable for inspecting the electro-fusion weld of this first end 3a of the sleeve with a sleeve end of a pipe element in which the sleeve 3 has been inserted and welded, as described below.

Thus, the ends furthest in the longitudinal direction from said second chamber 22 and said weld inspection device 23 are at substantially the same distance as the length L of the sleeve, the three elements 21, 22, 23 being suitable for being included inside said sleeve.

Figure 1B:
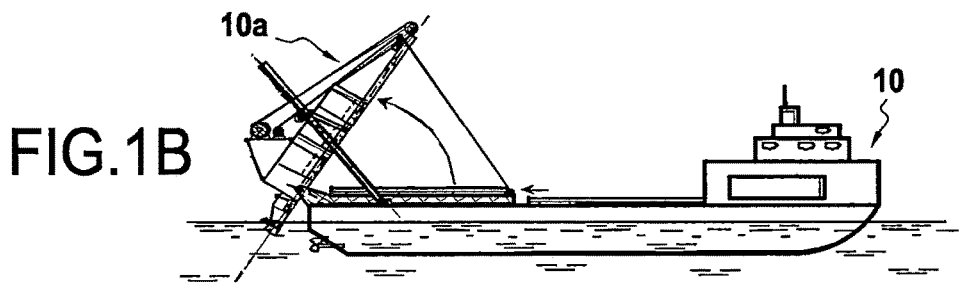
FIG. 1B is a side view of an installer ship fitted with a so-called "J-lay" tower.
Figure 1:
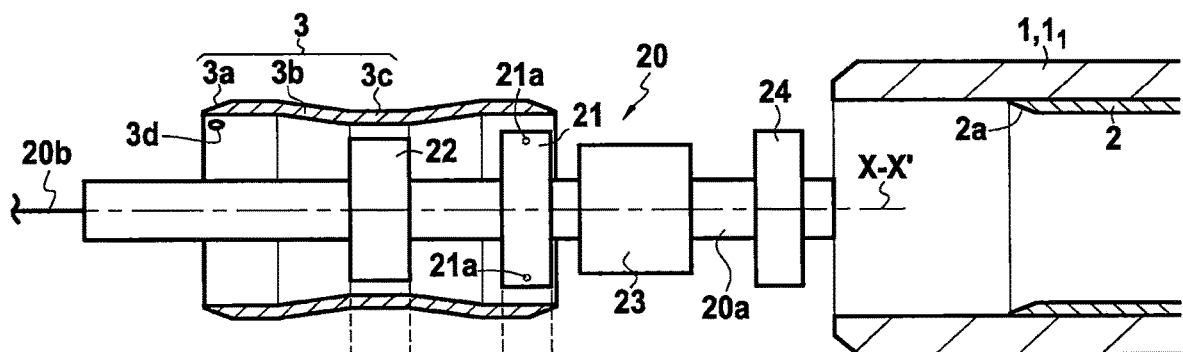
FIGS. 1 to 9 show various steps of installing and welding the sleeve 3 at one end of a pipe element using a device of the present invention, which is shown diagrammatically.
Figure 2:
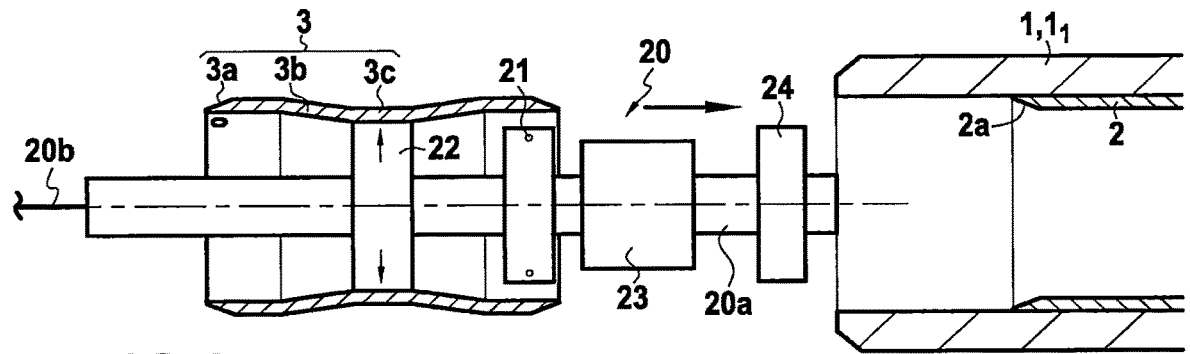
Figure 3:
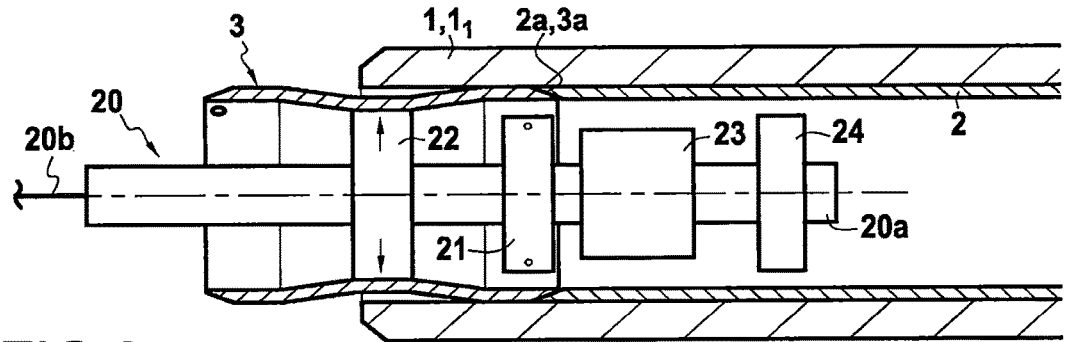
Figure 4:
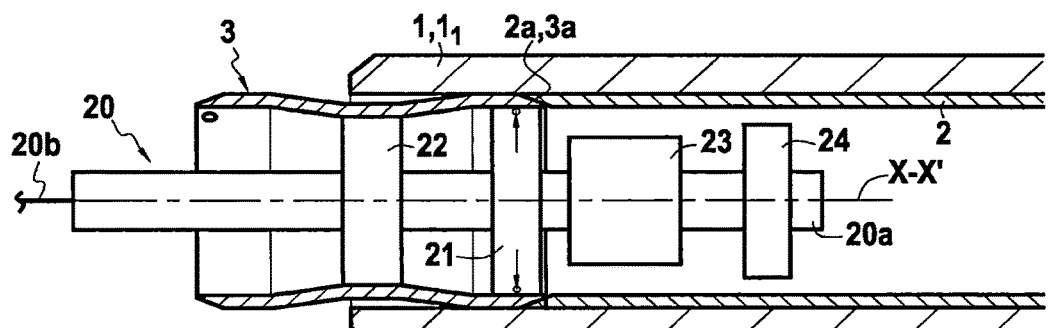
Figure 5:
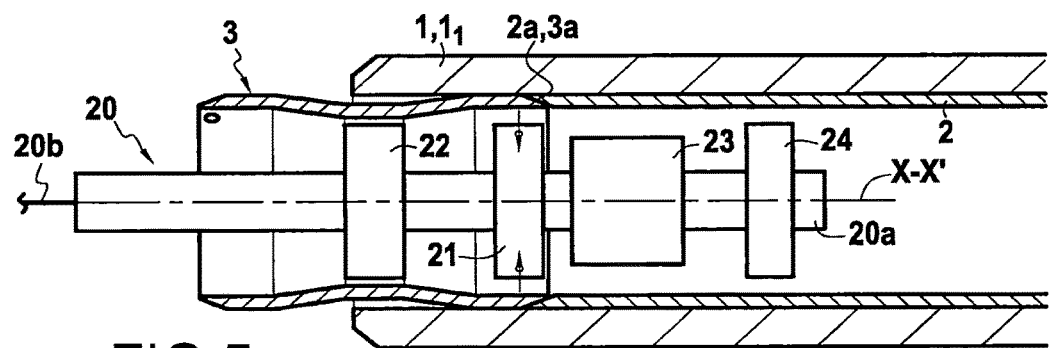

In FIG. 1, a device 20 of the present invention for installing the sleeve is shown inserted in such a manner that when it is fully inflated, the second inflatable chamber 22 presses against the wall of the constricted central portion 3c of the sleeve. The device 20 and the sleeve 3 are thus secured together and can be moved in horizontal translation towards the sleeve-free open end of a pipe element $1_1$ until coming into abutment against the end 2a of the lining 2 of the pipe element $1_1$, as shown in FIG. 3. At this moment, as shown in FIG. 4, the electrical connectors 21a of the first inflatable chamber 21 face corresponding electrical connectors 4a of the heater wire at one end of the sleeve, as shown in FIGS. 3 and 4. At this stage, the first inflatable chamber 21 can be inflated so as to press against the terminal portion 3a of the sleeve in abutment against the end 2a of the lining, and electricity is injected into the heater wire 4, thereby melting the entire zone 3a of the outer surface 3-2 of the sleeve that is covered by the heater wire, thus enabling the plane of contact between the tubular junction sleeve 3 at its end 3a to be welded by electro-fusion with the end 2a of the lining 2. The first chamber 21 is expanded with pressure serving to guarantee excellent compactness in the plane of melting and also to guarantee the absence of bubbles of air that would be harmful for good leaktightness at the melting surface.

Figure 6:
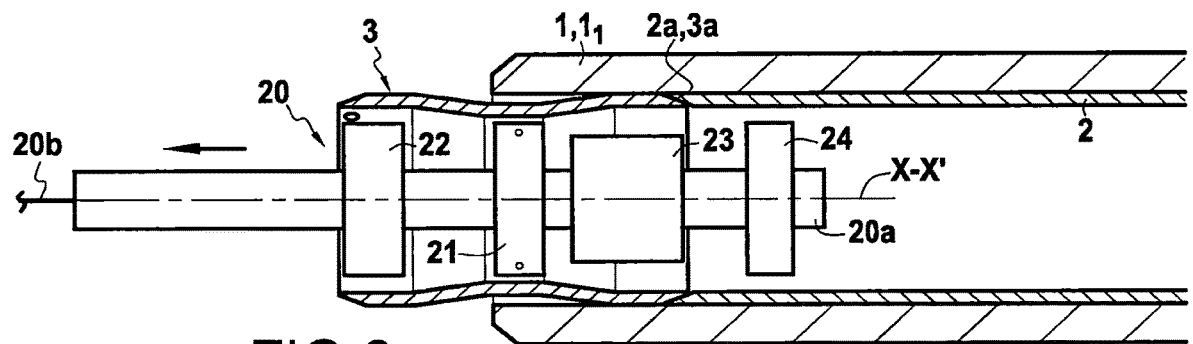

Thereafter, in order to perform the step of inspecting the quality of the weld, the first and second chambers 21 and 22 are deflated and they are moved in translation in the opposite direction until they reach the position shown in FIG. 6, where the weld inspection means 23 are facing the electrically-welded-together ends of the sleeve and of the internal lining of the pipe element $1_1$.

Said first and second inflatable chambers 21 and 22 in the deflated position remain relatively close to the walls of the sleeve such that it is easy for the device 20 to be guided in longitudinal translation inside the sleeve. Advantageously, this guidance may be performed manually or by a carriage or by other means for guiding movement in longitudinal translation.

Figure 7:
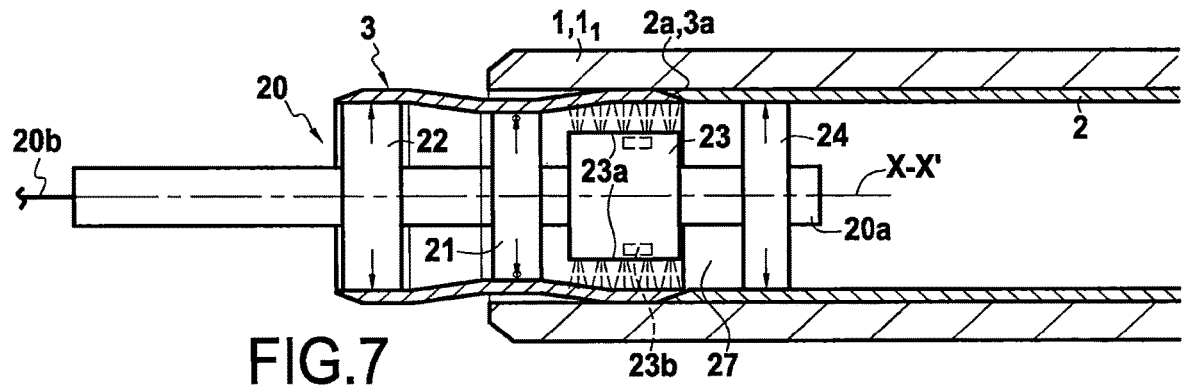
Figure 8:
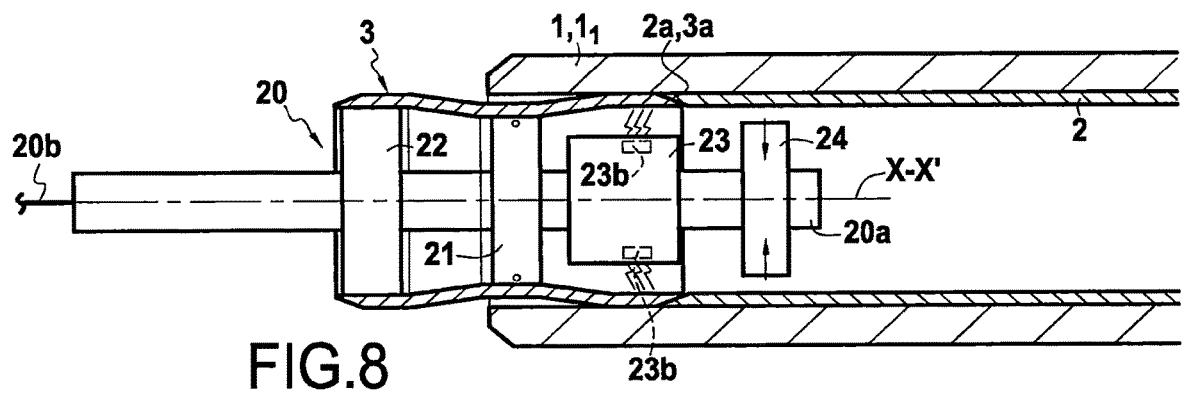
Figure 9:
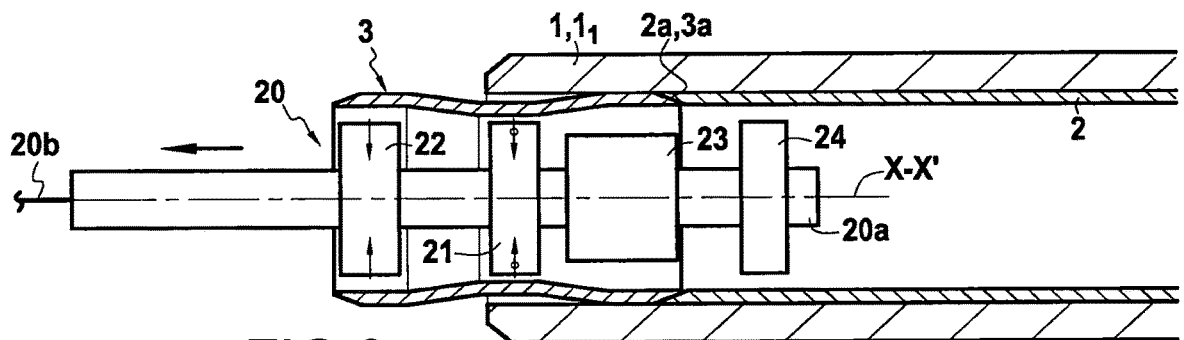
Figure 12:
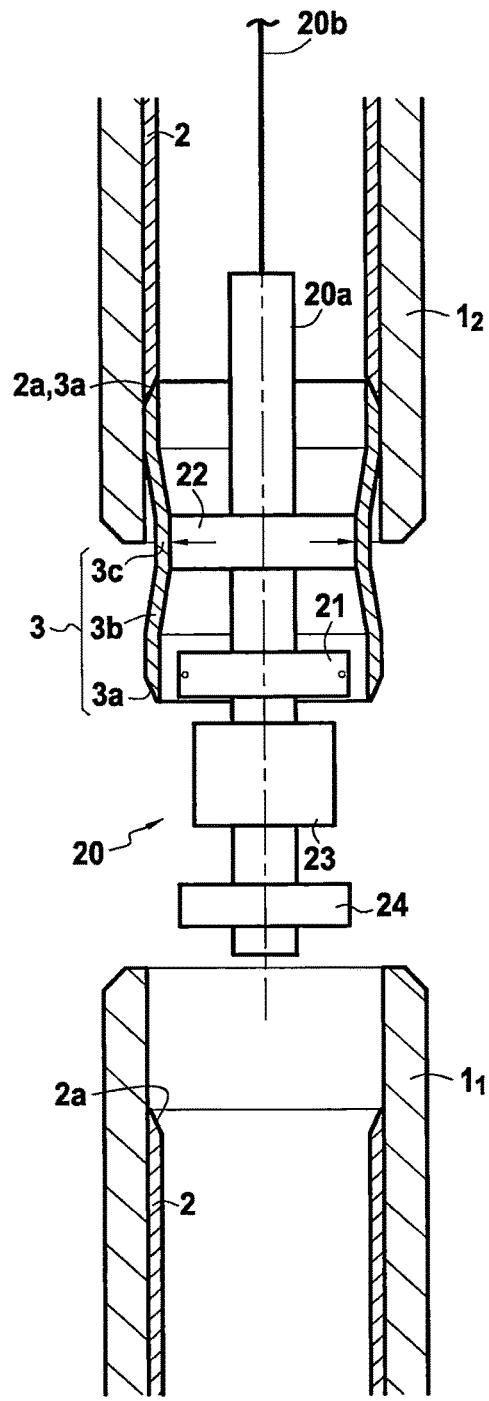

FIGS. 7 and 8 show the steps of inspecting the weld. In a first step, the device 20 is connected once more to the sleeve 3 by inflating the first inflatable chamber 21 and the second chamber 22 facing the constricted central portion 3c and the opposite terminal portion 3a of the sleeve 3. Thereafter, water is injected via the nozzles 23a against the electrically-welded end of the sleeve in the compartment 27 defined by the first chamber 21 and by the fully inflated third chamber 24 containing the means for emitting ultrasound and the weld inspection means 23. Thereafter, ultrasound waves are emitted with the ultrasound sensors 23b for verifying the quality of the weld performed by electrofusion. Water is injected simultaneously with emitting ultrasound locally in order to provide good transmission for the ultrasound wave. Once the weld has been inspected, it is possible to move the device 20 away in translation after previously deflating all of its inflatable chambers. A pipe element $1_1$ is thus made ready for laying, having a tubular junction sleeve 3 at one of its ends forming a male portion ready for being received in the female portion without a tubular junction sleeve of a second pipe element.

FIGS. 10 to 21 show how two unit lengths of lined pipe are assembled together during on-site installation performed on board a laying ship 10 that is fitted with a J-lay tower 10a, as shown in FIG. 1B. A new lined pipe element $1_2$ fitted with a tubular sleeve 3 at one of its ends is transferred in conventional manner from the horizontal position to the oblique position corresponding to the angle of inclination of the tower so as subsequently to be positioned on the axis of the terminal pipe element $1_1$ at the end of the string being laid. Said pipe element $1_2$ that is to be assembled is then moved axially towards the suspended terminal pipe element $1_1$. A portion of the sleeve 3 forming a male end of one of the pipe elements penetrates into the female end of the pipe element without a sleeve of the other pipe element that is to be assembled, until the terminal portion 3a of the sleeve comes into contact with the terminal portion 2a of the lining inside the pipe element. Since both pipe elements 3a are close to being vertical, a manipulator arm enables the terminal portion 3a of the sleeve to be inserted completely against the terminal portion of the lining so as to reach the configuration of FIG. 13, in which the two pipe elements $1_1$ and $1_2$ are held apart by a few millimeters, e.g. by means of said same manipulator arm (not shown), so as to make it possible in conventional manner to perform the welding 5 by means of an orbital welding robot 5a known to the person skilled in the art. The figures show the chamfered steel pipe walls that are a few millimeters apart during welding, and the screen 8 constituted by a mat of ceramic foam limiting the transfer of heat and protecting the thermoplastic sleeve throughout the duration of the welding process. On the right-hand side, the finished weld 5 is shown.

In an embodiment shown in FIGS. 10 to 21, a new terminal pipe element 12 is fitted with a tubular junction sleeve 3 at its bottom end, thereby forming a male end that is lowered towards the female top end of a sleeve-free first pipe element 11 forming the top terminal pipe element of a pipe that is being laid and that is held securely in suspension under a tower.

Figure 13:
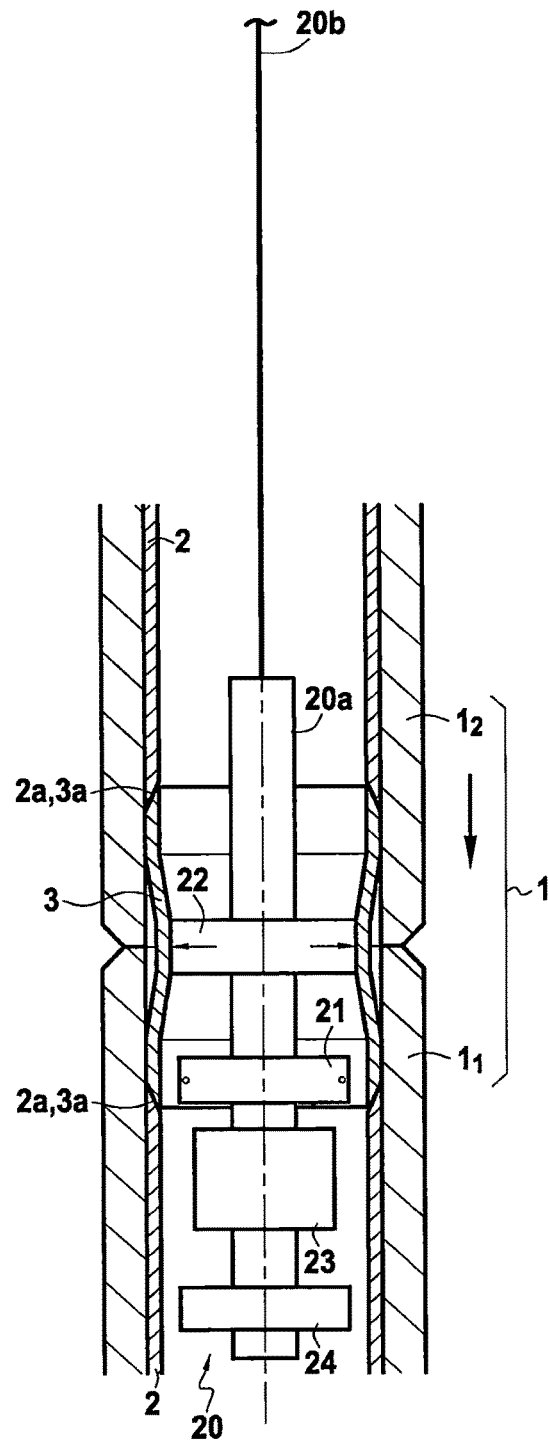
Figure 14:
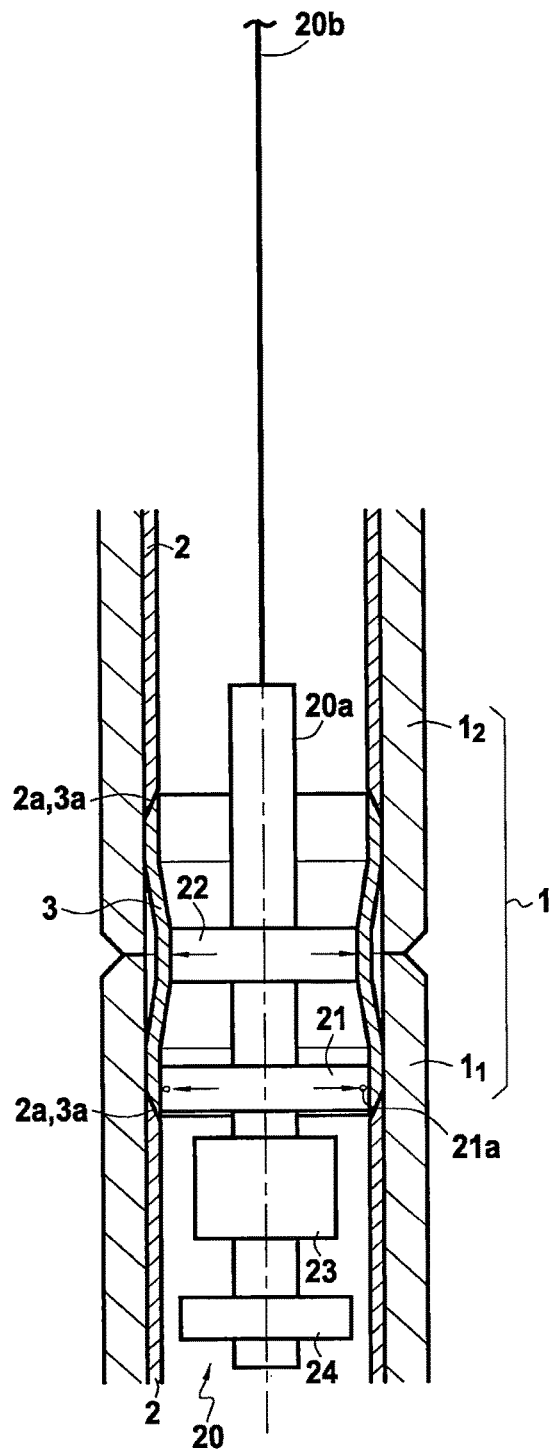
Figure 15:
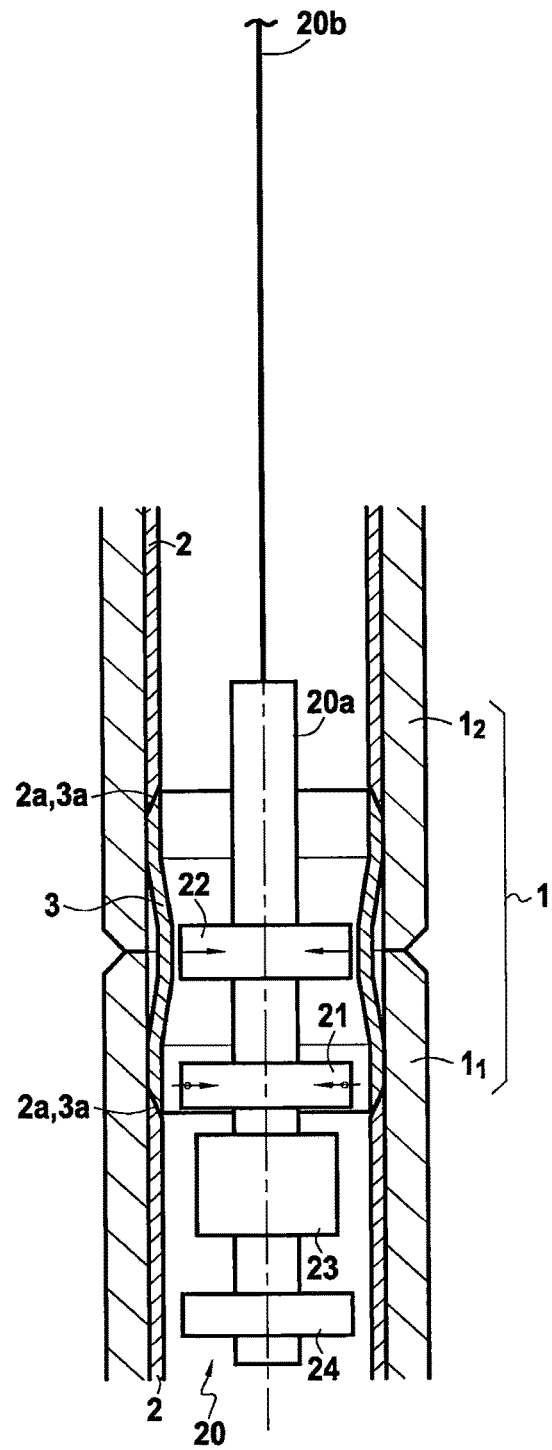

In a first step, the umbilical 20*b* is used to lower the device 20 for installing a sleeve so that the first inflatable chamber 21 is positioned facing the terminal portion 3*a* of the bottom end of the sleeve 3, with the connectors 21*a* facing the connectors 4*a* of the heater wire of the terminal portion 3*a*. In this way, the second inflatable chamber 22 faces the central portion 3*c* of the sleeve 3, as shown in FIG. 11. At this stage, the second chamber 22 is inflated so as to secure the device 20 and the sleeve 3 together, the device 20 now being lowered together with the pipe element 1$_2$ until the male end of the sleeve projecting from the end of the pipe element 1$_2$ is engaged inside the non-lined female portion of the pipe element 1$_1$, such that the terminal portions 3*a* of the sleeve 3 come into abutment against the terminal portion 2*a* of the lining 2 of the pipe element 1$_1$, as shown in FIG. 13.

At this stage, in order to perform electro-fusion, the first inflatable chamber 21 is inflated with the connectors 21*a* being connected with the connectors 4*a* of the heater wire on the inside wall of the sleeve, and electricity is injected into the heater wire so as to perform electro-fusion between the terminal portion 3*a* of the sleeve 4 and the terminal portion 2*a* of the lining 2, the electricity being conveyed in a duct inside the umbilical 20*b*.

Figure 16:
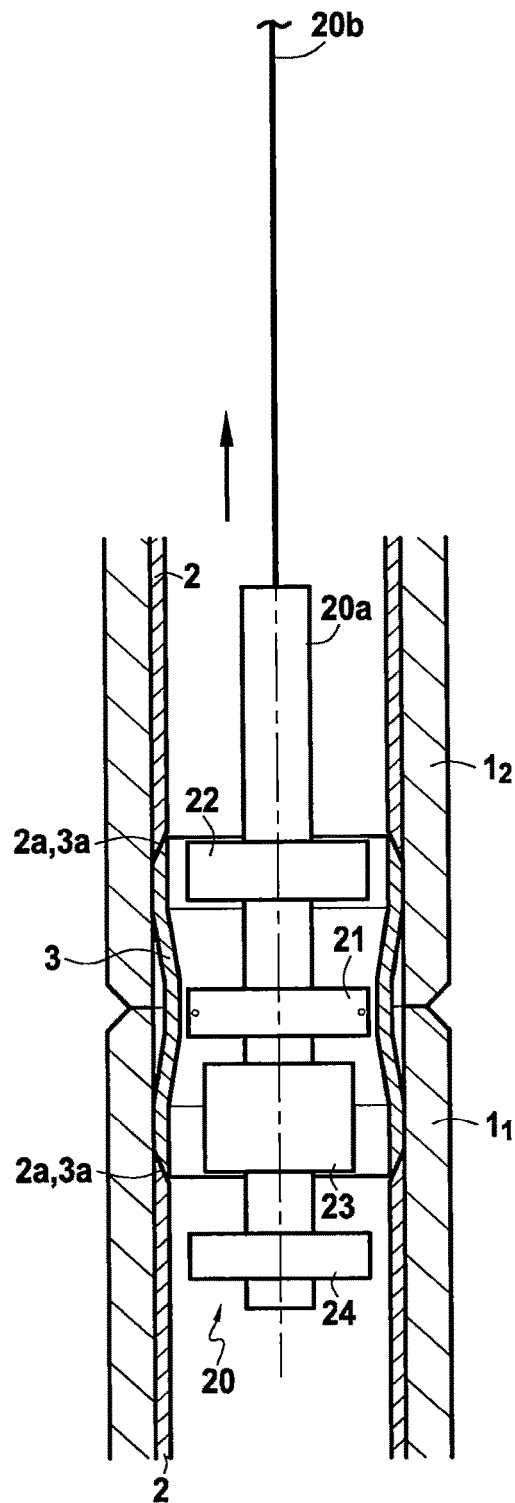
Figure 17:
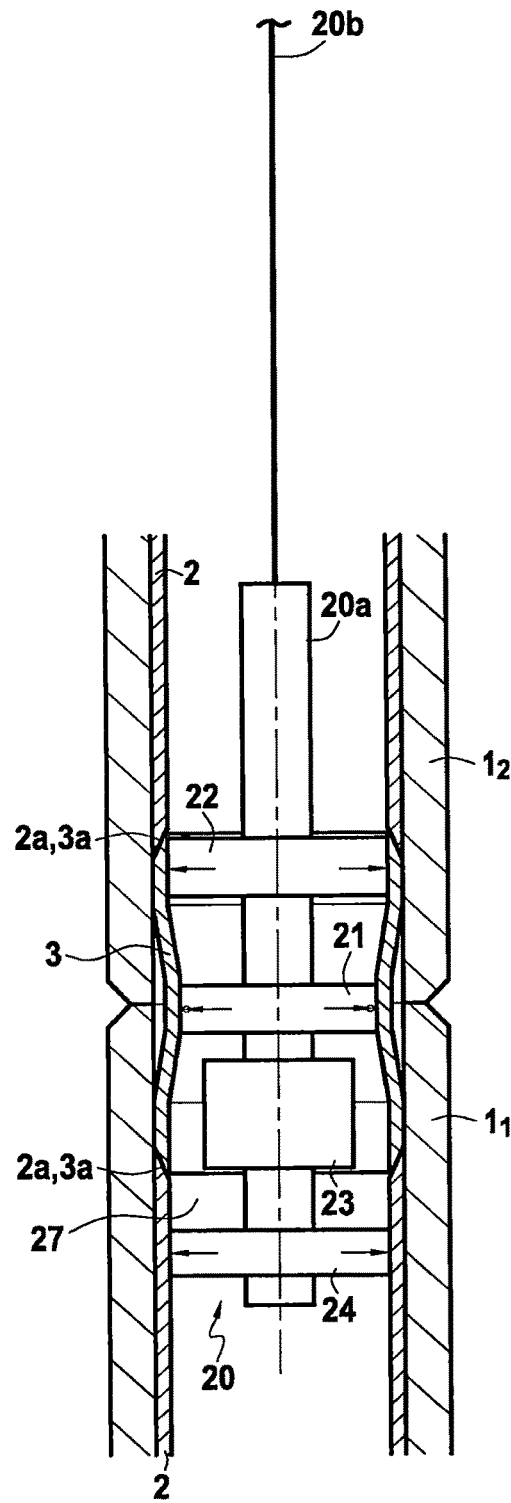
Figure 18:
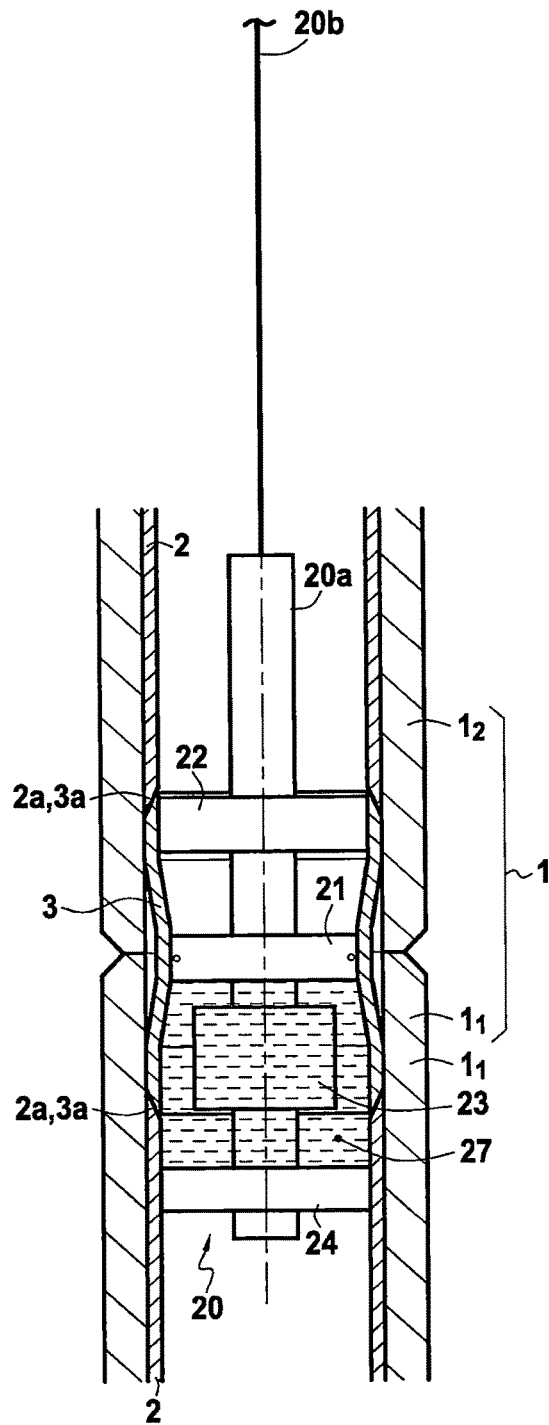
Figure 19:
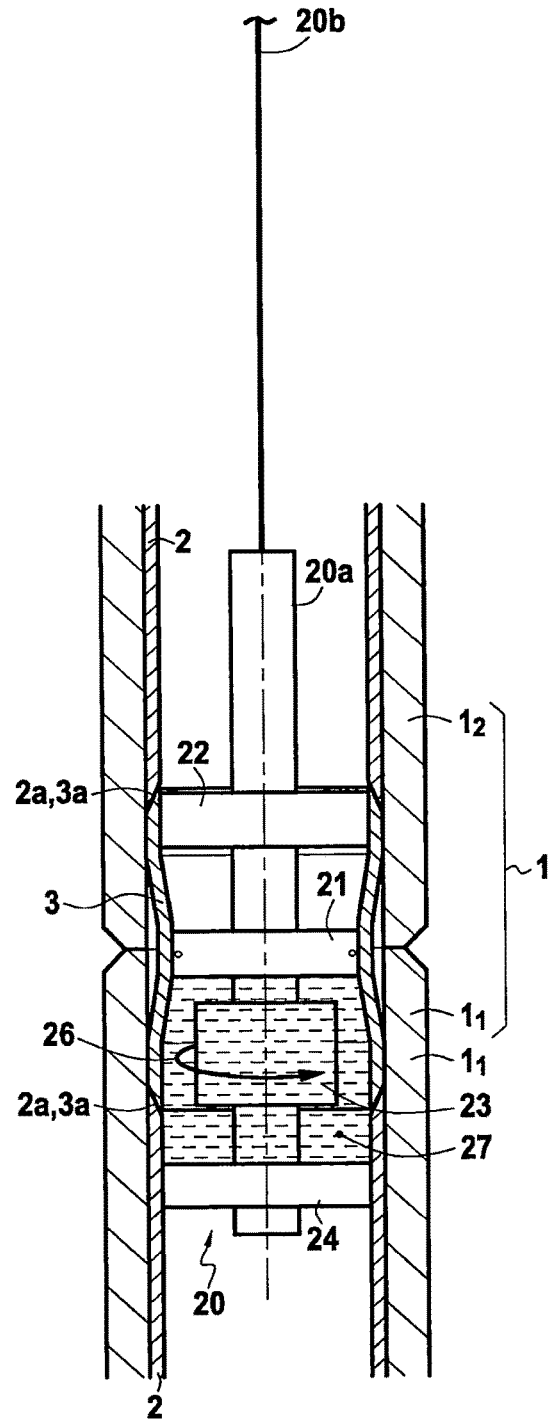
Figure 20:
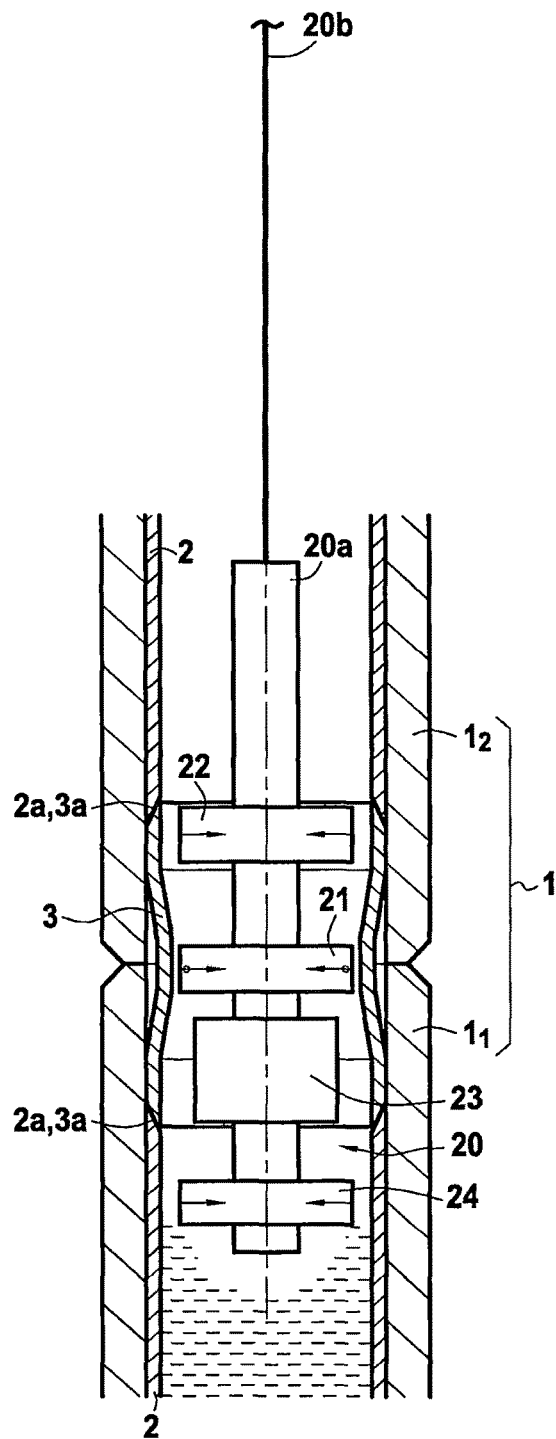
Figure 21:
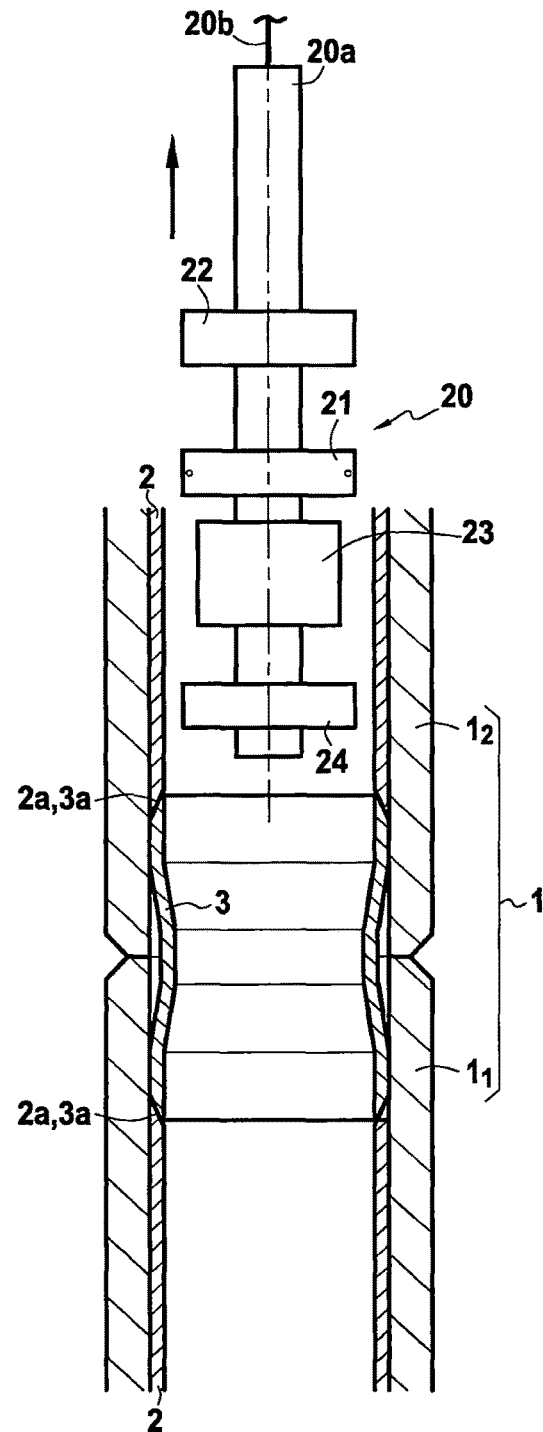

Thereafter, in order to inspect the weld, the two chambers 21 and 22 are deflated and the device 20 is raised in longitudinal translation XX' so that, the weld inspection means 23 face the previously electro-welded ends 2*a*-3*a*, as shown in FIG. 16. At this stage, it is now the first inflatable chamber 21 that faces the central portion 3*c* of smaller diameter of the sleeve 3, while the second inflatable chamber 22 faces the top terminal portion 3*a* of the sleeve that has already been electro-welded before lowering the element 1$_2$ (on the deck of the ship). At this stage, the device 20 is secured once again with the sleeve 3 by inflating both chambers 21 and 22 against the inside wall of the sleeve 3. Thereafter, the third inflatable chamber 24 is expanded so as to make a leaktight wall at the bottom end of the mandrel 20*a* to define a leaktight compartment 27 between the wall 24 and the first inflatable chamber in the expanded position 21. Before inspecting the weld, water is injected into the compartment 27 via the nozzles 23*a*. The water is conveyed inside the umbilical 20*b*. As shown in FIG. 19, the electro-fusion zone is inspected by emitting soundwaves via probes 23*b* placed against the plastic. Thereafter, the various inflatable walls 21, 22, and 24 can be deflated and the device 20 can be raised for performing a subsequent assembly of a new pipe element.

Figure 22:
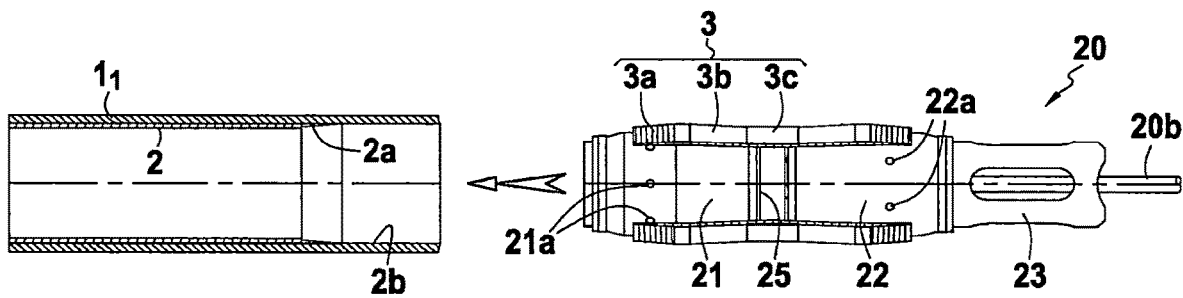
FIGS. 22 and 23 show a device 20 for installing a sleeve that comprises two chambers suitable for performing electro-fusion.
Figure 23:
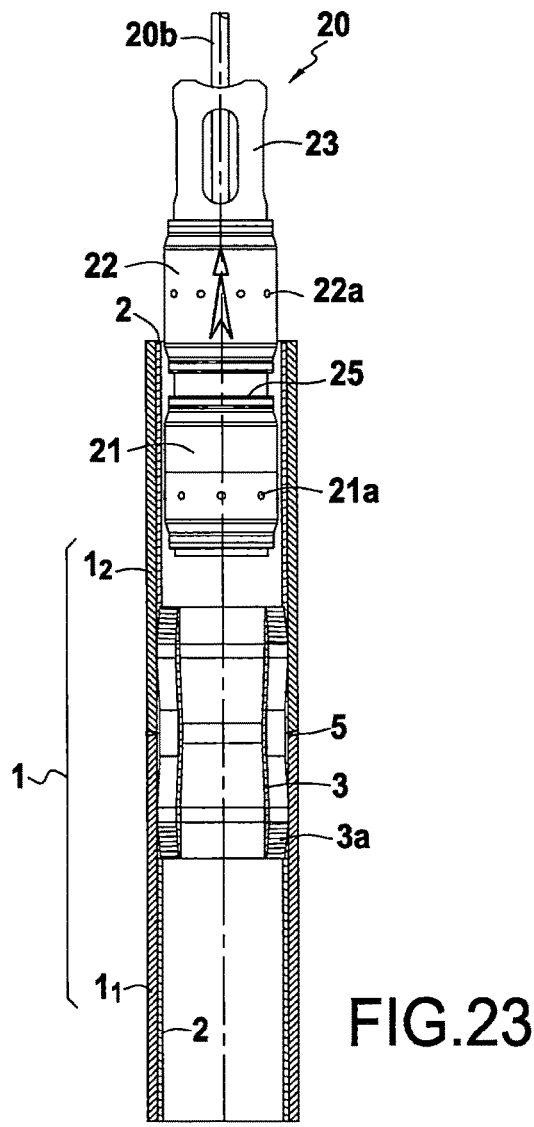

FIGS. 22 and 23 show an embodiment in which the two chambers 21 and 22 are fitted with electrical connectors 21*a* and 22*a* that are placed in such a manner as to enable them to be positioned simultaneously facing electrical connectors 4*a* at the two ends of a single sleeve 3, the two chambers 21 and 22 together being of a length greater than the length of the sleeve 3 so that the two chambers can coincide with and press against both ends of the sleeve simultaneously.

Alternatively, it is possible to lower a new pipe element 1$_2$ already fitted with a tubular junction sleeve 3 at its bottom top end, but having its sleeve-free bottom end thus forming a female end of said new pipe element which is lowered towards the male top end of a first pipe element 1$_1$ fitted with a tubular junction sleeve 3 at its top end, this first pipe element 1$_1$ forming the top terminal pipe element of a pipe that is being laid and that is suspended securely under a tower.

The invention claimed is:

1. A device suitable for installing a tubular junction sleeve inside an end of a first pipe element made of steel and internally lined with a thermoplastic material, and suitable for butt-joining the end of the first pipe element fitted with said tubular junction sleeve and an end of a second pipe element having internal lining of thermoplastic material, said ends of the two pipe elements abutting for welding together, said tubular junction sleeve having at each end a terminal tubular wall portion, at least one of said terminal tubular wall portions having a Joule-effect heater wire arranged at the outer surface of said terminal tubular wall portion suitable for creating by heating a zone of contact made leaktight by melting between the materials constituting at least a part of said terminal tubular wall portion and a terminal portion of said internal lining where they are in contact with each other, said device comprising:
a mandrel extending in a longitudinal direction supporting on the outer surface of said mandrel at least a first inflatable chamber having a first peripheral wall that is radially expandable by inflation, said first peripheral wall having at least one first electrical connector suitable for being connected to one end of said Joule-effect heater wire, and said mandrel also having an umbilical comprising at least one compressed air feed duct for inflating said first inflatable chamber and an electrical power supply duct connected to said first electrical connector,
wherein said mandrel also supports on said outer surface of said mandrel a second inflatable chamber having a second peripheral wall that is radially expandable by inflation and spaced apart from said first inflatable chamber in said longitudinal direction, and said mandrel also supports a weld inspection device, said umbilical passing inside said mandrel and including ducts for electrically powering said weld inspection device.

2. The device according to claim 1, wherein said weld inspection device is arranged in the longitudinal direction of the mandrel upstream or downstream relative to said first and second inflatable chambers.

3. The device according to claim 1, wherein said weld inspection device comprises:
at least one ultrasound probe; and
at least one water injection nozzle fed with water by a duct passing in said umbilical.

4. The device according to claim 3, wherein at least one of said ultrasound probe or said water injection nozzle suitable for being turned facing the terminal tubular wall portions about a turning axis arranged on a longitudinal axis of the mandrel.

5. The device according to claim 1, wherein said mandrel also supports a reversible shutter for shutting a passage between the mandrel and an inside wall of the tubular junction sleeve or of the internal lining of the pipe elements, said shutter being arranged in said longitudinal direction of the mandrel so that said weld inspection device is arranged between said reversible shutter and at least one said first or second inflatable chamber.

6. The device according to claim 5, wherein said reversible shutter is constituted by a third inflatable chamber having a peripheral wall that is radially expandable by inflation.

7. The device according to claim 1, wherein said expandable second peripheral wall of said second inflatable chamber includes at least one second electrical connector suitable for being connected to an end of said Joule-effect heater wire.

8. The device according to claim 1, wherein said first and second inflatable chambers extend over respective lengths L1 and L2 and are spaced apart by a distance d in the longitudinal direction of the mandrel such that when said first inflatable chamber is radially expanded to press against one of the terminal tubular wall portions, the second inflatable chamber is in a facing position and can press against a portion of a tubular inside wall of said tubular junction sleeve.

9. The device according to claim 1, wherein each of said inflatable chambers is formed by a flexible or semi-rigid tubular envelope of circular cross-section arranged around said mandrel which is cylindrical, wherein circular edges of each said tubular envelope join an outer wall of said mandrel in such a manner that under the effect of said inflatable chambers being inflated said tubular envelope takes on a convex bulging shape forming a radially expanded wall of said inflatable chambers.

10. A method of installing a tubular junction sleeve at one end of a first pipe element having an internal lining made of thermoplastic material, the method comprising:
   using the device of claim 1 in order to fasten said tubular junction sleeve to a terminal portion of said internal lining, by using a Joule-effect heater wire arranged at an outer surface of a first terminal portion of the tubular junction sleeve, to create a leaktight contact zone by melting together materials constituting at least parts of said first terminal portion of the tubular junction sleeve and of said terminal portion of said internal lining.

11. The method according to claim 10, further comprising the following steps:
   i.1) positioning said device inside said tubular junction sleeve in such a manner that at least said first inflatable chamber is in position facing said first terminal portion of the tubular junction sleeve with said first electrical connector facing an end of said Joule-effect heater wire, said second inflatable chamber facing an inside wall of a running portion of the tubular junction sleeve, and inflating at least said second inflatable chamber so as to secure the device with said tubular junction sleeve by pressing the expandable second peripheral wall of said second chamber against said inside wall of said tubular junction sleeve, resulting thereby in an assembly of the tubular junction sleeve and said device;
   i.2) moving the resulting assembly of the tubular junction sleeve and said device in the longitudinal direction and inserting said assembly inside a sleeve-free open end of said first pipe element until said first terminal portion of the tubular junction sleeve is in contact with said terminal portion of the internal lining of said sleeve-free open end of said first pipe element;
   i.3) inflating said first inflatable chamber to press it against the inside wall of said first terminal portion of the tubular junction sleeve so that said first electrical connector is connected to the end of a said Joule-effect heater wire;
   i.4) electrically powering said Joule-effect heater wire while simultaneously exerting pressure from said first terminal portion of the tubular junction sleeve against said terminal portion of the internal lining that are in contact with each other by inflating said first inflatable chamber in order to implement a weld zone by electro-fusion of the materials constituting at least parts of said first terminal portion of the tubular junction sleeve and of said terminal portion of said internal lining that are in contact with each other;
   i.5) deflating said first and second inflatable chambers and moving said device in such a manner that said weld inspection device is placed facing said first terminal portion of the tubular junction sleeve corresponding to said zone of welding by electro-fusion;
   i.6) inflating again the first and second inflatable chambers so that they press against the inside wall of the tubular junction sleeve and become secured thereto, and actuating said weld inspection device to inspect said weld; and
   i.7) deflating said first and second chambers in order to remove said device.

12. A method of making a pipe by using the device according to claim 1, by assembling first and second pipe elements, each including an internal lining, with a tubular junction sleeve inserted and fastened to one end of said first pipe element with a part projecting therefrom, the projecting part of said tubular junction sleeve defining a male end of said first pipe element suitable for being assembled with a sleeve-free end defining a female end of said second pipe element, said tubular junction sleeve having at each of its ends a terminal tubular wall portion, an outer surface of at least one of said terminal tubular wall portions having a Joule-effect heater wire suitable for creating, by heating, a contact zone made leaktight by melting together materials constituting at least parts of said terminal tubular wall portion and of a terminal portion of said internal lining that are in contact with each other, the method comprising the following steps:
   a) inserting said device inside said first pipe element so that said first inflatable chamber is arranged with said first electrical connector facing an end of said Joule-effect heater wire, and fastening said device inside said tubular junction sleeve by inflating said second inflatable chamber against an inside wall of said tubular junction sleeve;
   b) before or after step a) forcibly inserting the projecting part of said male end of said first pipe element into the female end of the second pipe element until said terminal tubular wall portion of said male end comes into contact with said terminal portion of the internal lining of said female end of said second pipe element to be assembled therewith;
   c) butt-welding the ends of the two pipe elements together;
   d) inflating said first inflatable chamber and connecting said first electrical connector to the end of the Joule-effect heater wire and electrically powering said Joule-effect heater wire, while simultaneously exerting pressure from said terminal tubular wall portion against said terminal portion of the internal lining in order to make a weld zone by electro-fusion in at least a fraction of the interface between surfaces of said terminal tubular wall portion and said terminal portion of the internal lining that are in contact with each other in order to make a contact zone that is made leaktight by melting; and
   e) deflating said first and second inflatable chambers.

13. The method according to claim 12, further comprising the following steps:
- step a) further comprises:
  - a.1) using a pipe-laying tower of a laying ship to lower said first pipe element fitted with said tubular junction sleeve into proximity of the end of the second pipe element that is partially immersed at the bottom of the pipe-laying tower; and
  - a.2) lowering said device into said first pipe element with said first and second inflatable chambers at least partially deflated; and
- following the deflating of said first and second inflatable chambers in step e), moving said mandrel so that said weld inspection device is placed facing said terminal tubular wall portion which is electro-welded;
- inflating the first and second inflatable chambers so that they press against the inside wall of the tubular junction sleeve and are secured thereto; and
- actuating said weld inspection device in order to inspect said weld.

14. The method according to claim 13, wherein weld inspection further comprises:
- actuating a reversible shutter to form a leaktight compartment defined between said first inflatable chamber by closing a passage inside the pipe, said leaktight compartment containing said weld inspection device;
- filling said leaktight compartment with water before actuating said weld inspection device to inspect said weld; and
- weld inspection, actuating said reversible shutter to open the leaktight compartment.

* * * * *